(12) United States Patent
Munro et al.

(10) Patent No.: US 9,056,127 B2
(45) Date of Patent: Jun. 16, 2015

(54) HYDROGEL COMPOSITION BASED ON CO-POLYMER CARRYING MULTIPLE PENDANT SULPHONIC GROUPS FOR USE AS A WOUND DRESSING

(71) Applicant: FIRST WATER LIMITED, Marlborough Wiltshire (GB)

(72) Inventors: Hugh Semple Munro, Chipping Campden Warwickshire (GB); Nicholas Boote, Faringdon Oxon (GB)

(73) Assignee: FIRST WATER LIMITED (GB)

( * ) Notice: Subject to any disclaimer, the term of this patent is extended or adjusted under 35 U.S.C. 154(b) by 87 days.

(21) Appl. No.: 13/734,457

(22) Filed: Jan. 4, 2013

(65) Prior Publication Data

US 2013/0121952 A1    May 16, 2013

Related U.S. Application Data

(63) Continuation of application No. 12/812,926, filed as application No. PCT/GB2009/000128 on Jan. 16, 2009, now abandoned.

(60) Provisional application No. 61/021,771, filed on Jan. 17, 2008.

(51) Int. Cl.
| | |
|---|---|
| *A61K 31/795* | (2006.01) |
| *A61L 15/00* | (2006.01) |
| *A61L 26/00* | (2006.01) |
| *A61L 15/60* | (2006.01) |
| *C08F 220/58* | (2006.01) |

(52) U.S. Cl.
CPC ........... *A61K 31/795* (2013.01); *A61L 26/0014* (2013.01); *A61L 15/60* (2013.01); *A61L 26/008* (2013.01); *C08F 220/58* (2013.01)

(58) Field of Classification Search
None
See application file for complete search history.

(56) References Cited

U.S. PATENT DOCUMENTS

| 6,447,798 B1 | 9/2002 | Munro et al. |
| 2002/0035320 A1 | 3/2002 | Munro et al. |

FOREIGN PATENT DOCUMENTS

| EP | 1559437 A2 | 8/2005 |
| WO | 93/04691 A1 | 3/1993 |
| WO | 93/10795 A1 | 6/1993 |
| WO | 96/02270 A1 | 2/1996 |
| WO | 97/24149 A1 | 7/1997 |
| WO | 97/34937 A1 | 9/1997 |
| WO | 00/06214 A1 | 2/2000 |
| WO | 00/06215 A1 | 2/2000 |
| WO | 00/07638 A1 | 2/2000 |
| WO | 00/46319 A1 | 8/2000 |
| WO | 00/65143 A1 | 11/2000 |
| WO | 01/96422 A1 | 12/2001 |
| WO | 2004/052415 | 6/2004 |
| WO | 2007/007115 A2 | 1/2007 |

OTHER PUBLICATIONS

Hampton, "A small study in healing rates and symptom control using a new sheet hydrogel dressing", Journal of Wound Care, 2004, pp. 297-300.
Oxyzyme system, www.wounds-uk.com/posterabstracts2003.pdf.

*Primary Examiner* — Kevin S Orwig
(74) *Attorney, Agent, or Firm* — Nixon Peabody LLP

(57) ABSTRACT

The present invention provides a hydrogel composition, preferably for the treatment of wounds, comprising a hydrophilic co-polymer carrying multiple pendant anionic groups, wherein the polymer is derived from a first monomer and a second monomer, wherein both monomers have an octanol:water partition coefficient LogP value of less than 0, and, the LogP value of the first monomer is greater (more positive) than the second monomer. The difference between the LogP value for the two monomers is preferably less than 2. The weight ratio (w/w) of the first monomer/second monomer in the hydrogel composition is preferably equal to or more than about 1. The pendant anionic groups may be sulphonyl groups, e.g. sulphonic acid groups or salts thereof. The anionic group in both first and second monomers may be in salt form and the counterion for both monomers is preferably the same.

3 Claims, 3 Drawing Sheets

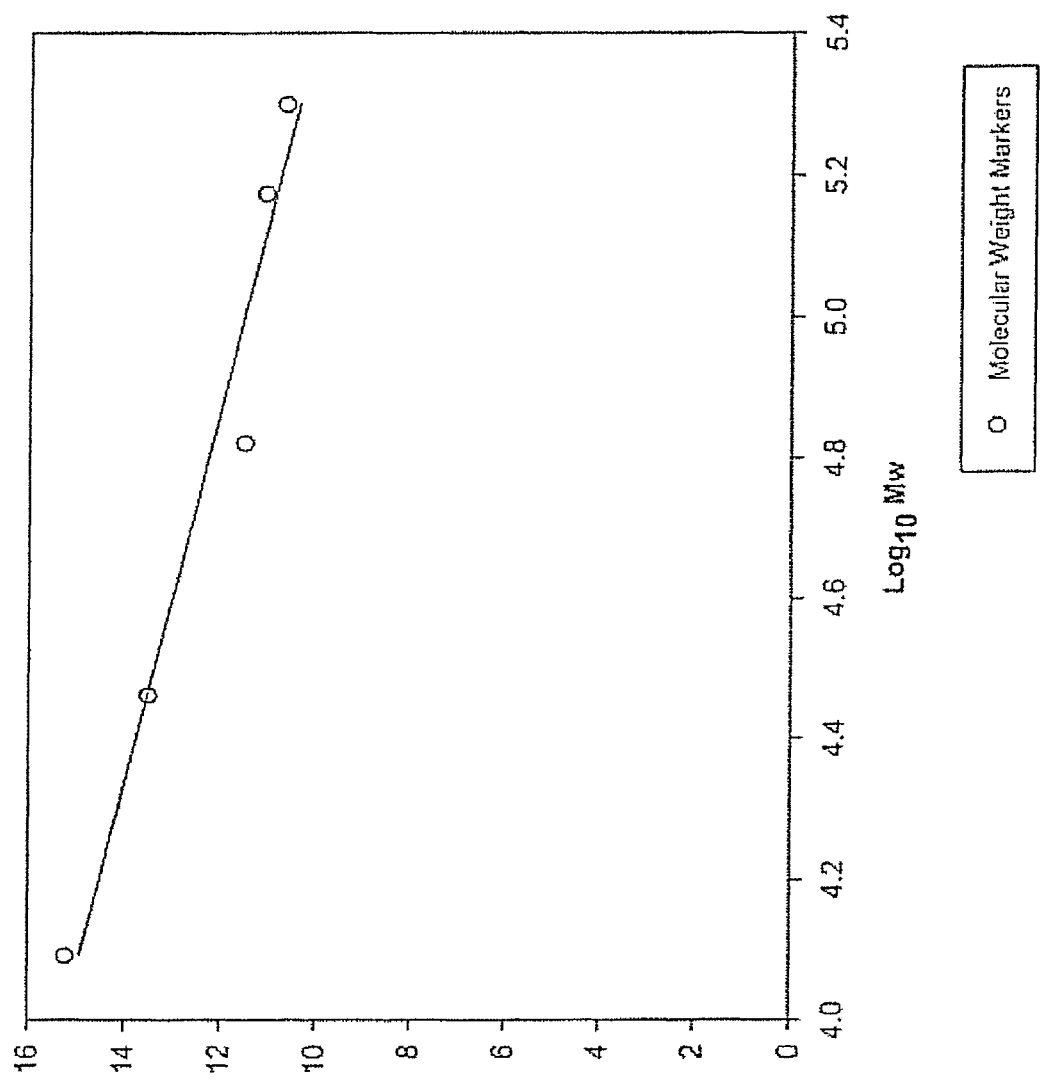
Fig 1; Retention Time (mins) versus Log₁₀ Molecular Weight

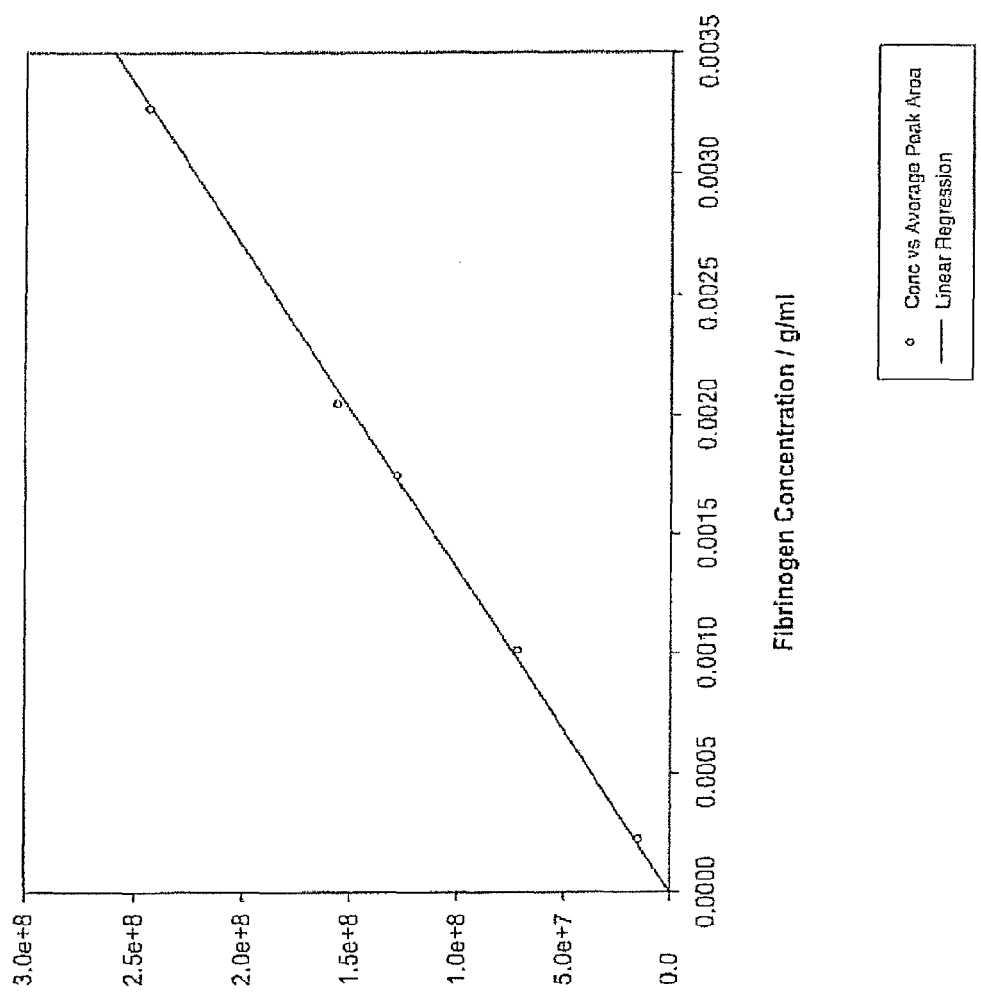
Fig 2: Peak Area (units) versus Fibrinogen Concentration (g/ml). Error bars are standard deviation.

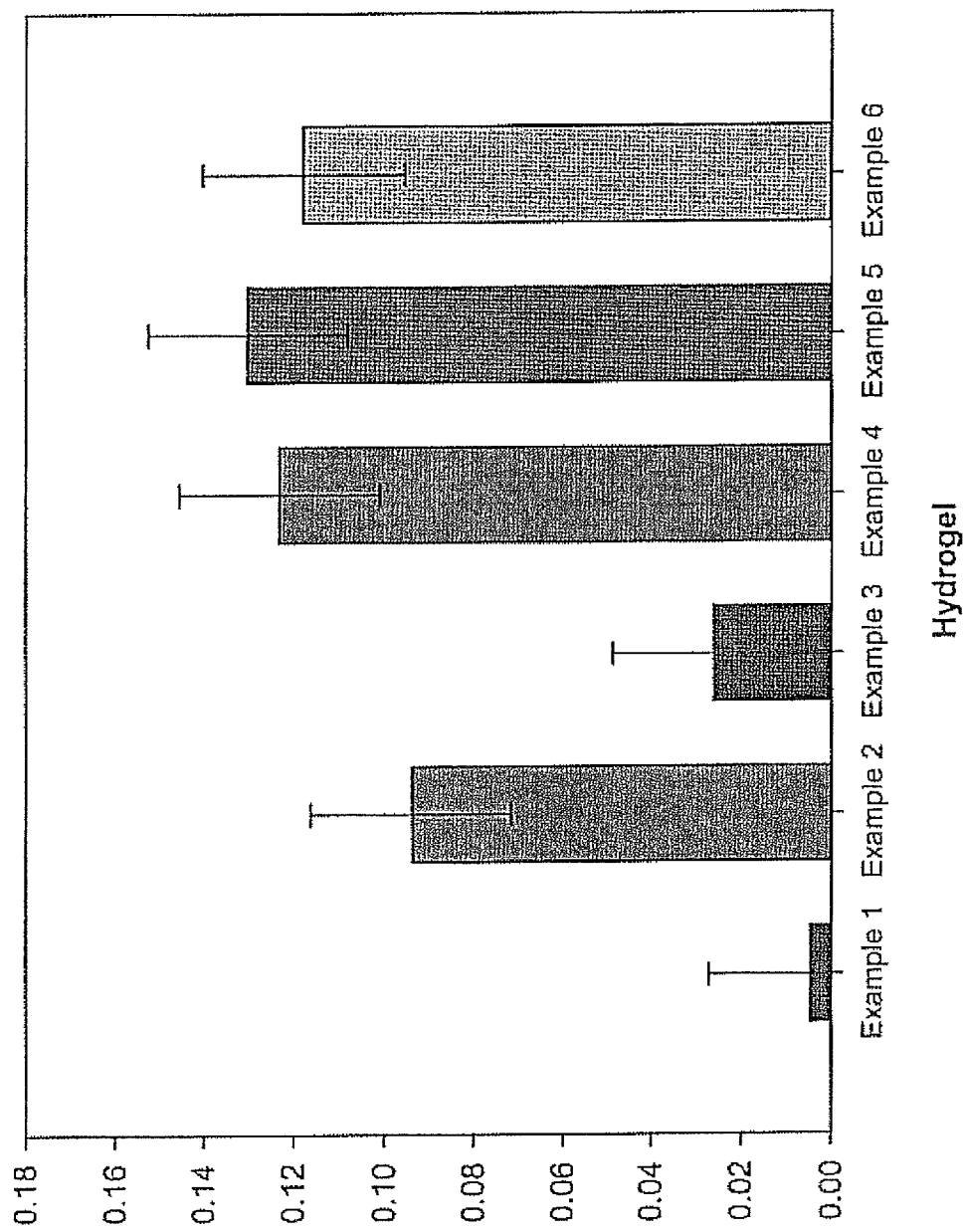
Fig 3. Fibrinogen in supernatant fluid (g/100ml) after 22hrs exposure to six different hydrogels

HYDROGEL COMPOSITION BASED ON CO-POLYMER CARRYING MULTIPLE PENDANT SULPHONIC GROUPS FOR USE AS A WOUND DRESSING

CROSS REFERENCED APPLICATIONS

This is a Continuation Application of U.S. application Ser. No. 12/812,926, filed Oct. 27, 2010, which is a National Phase Entry under 35 U.S.C. §371 of International Application PCT/GB2009/000128, filed 16 Jan. 2009, which claims the benefit under 35 U.S.C. 119(e) of U.S. Provisional Application Ser. No. 61/021,771 filed 17 Jan. 2008, the contents of which are incorporated herein by reference in their entirety.

FIELD OF THE INVENTION

The present invention relates to a hydrogel co-polymer composition and its uses, particularly those including use as a wound dressing, and for the treatment of pain and/or inflammation.

The present invention develops the concept of "Pro-Ionic™" treatment of wounds introduced in our PCT patent application No. PCT/GB2006/002632 (publication no. WO/2007007115), the contents of which are incorporated herein by reference, in which a hydrogel dressing in contact with the wound provides in use a controlled-moisture environment for the wound and selective uptake of proteins and ions from the wound, to stimulate and/or maintain the wound healing process.

More particularly, according to the present invention the hydrogel has surprisingly been found to modulate the activity and or concentration of proteins in biological environments, for example in skin lesions, particularly chronic ulcerous skin lesions, which is believed to assist in the healing process of an affected area and/or have one or more of the beneficial effects mentioned below.

Without wishing to be bound by theory, the hydrogel is believed to mimic the function of natural glycosminoglycans of a normal healing wound, and in particular certain sulphonated glycosaminoglycans of the extracellular matrix such as heparin, using a moist wound healing environment where the water levels are controlled to avoid the disadvantages of too much or too little moisture. In particular it is believed that the hydrogel comprising two or more structurally different multiple strongly hydrophilic pendant anionic groups counter balanced by one or more cations mimic some of the functions of the structurally different strongly hydrophilic groups found in natural glycosoaminoglycans and in particular certain sulphonated glycosaminoglycans such as heparin. In the case of chronic wounds, the hydrogel suppresses the inflammation processes that are associated chronic failure of the wound to heal and thus stimulates and/or maintains the normal healing process. In the case of acute wounds, the dressing suppresses a tendency towards chronic failure to heal, and stimulates and/or maintains the normal healing process.

The hydrogel used is a certain type of hydrous hydrophilic (ionic) polymer, described in more detail below. The ions covalently linked to the polymer molecule are generally anions; the cations are generally present as counterions (generally mono- or di-valent cations such as metal ions or primary or substituted ammonium ions). The hydrogel, including its associated water and ions, may have one or more, for example simultaneously any two or more, of the following beneficial effects, without the need for other specific bioactive agents, namely: (1) reduction in inflammation and/or the healing of a wound, (2) reduced wound odour, (3) beneficial wound debridement, (4) beneficial skin conditioning, (5) beneficial pain relief, and (6) in combination, beneficial suppression of the processes which lead to, and/or maintain, a chronic wound with beneficial wound bed stimulation and/or maintenance of the healing process (see also WO2007/007115). Preferably, the beneficial effects on the wound include simultaneously one or more, more preferably two or more, more preferably three or all, of effects (1) to (6).

BACKGROUND OF THE INVENTION

Lesion Healing Process

The normal process of healing of a skin lesion (wound) typically proceeds via four distinct sequential stages or phases, namely haemostasis, inflammation, proliferation and maturation.

Haemostasis is the vascular response stage, occurring immediately after the insult is suffered, and normally lasts for up to about three days in humans. The wound may bleed initially, and the blood then clots.

Inflammation normally arises about one day after the insult, and typically continues until about six days after the insult. Inflammation involves one or more of redness, heat, swelling and pain. The wound starts to exude fluid, which serves to remove debris, and proteases are released into the wound area. White blood cells and macrophages begin to congregate in the lesion zone, the former to clear debris and the latter for phagocytosis and to release growth factors to stimulate fibroblasts. During this phase the extracellular matrix is constructed.

Proliferation normally arises about four days after the insult, and typically continues until about 21 days after the insult, and involves the gradual formation of granulation tissue to fill the lesion zone. The redness, heat, swelling and pain gradually subside during this phase. For these reasons, granulation and contracture are sometimes identified as sub-phases within the proliferation phase. During proliferation, the macrophages stimulate vascular endothelial growth factor (VEGF) to stimulate new blood vessel growth, and the concentration of fibroblasts increase, producing collagen for the new tissues.

The maturation phase normally arises about 21 days after the insult, and typically continues for several weeks, months or even years thereafter. Maturation involves contraction of the wound, growth of new epithelial tissue covering the wound, and possibly scar formation. During this phase myofibroblasts develop from the fibroblasts and the collagen fibres gradually mature and become relatively more organised.

Generally, different parts of a wound heal at different rates, so that it is common for some parts of a normal wound to be at a more advanced stage of healing than others.

The above timescale of a normal wound is provided for general illustration only, and is not definitive for all normal wound healing. The present invention is not limited by any requirement that the normal wound healing process must follow any particular pathway or timescale.

Chronic Ulcerous Skin Lesions

Chronic skin lesions arise when a skin wound generally fails to follow an appropriate timely healing process to achieve the normal sustained and stable anatomic and functional integrity of the healed tissue. Generally speaking, a skin lesion which has failed to make at least substantial progress towards healing within a period of at least about three months, or which has become stable in a partially healed state for more than about three months, could be categorised as chronic, although even this general guide is not an absolute marker as the age and fitness of the patient, as well as other factors such as diseases or disorders suffered by the patient (for example, circulatory disorders), can significantly lengthen the normal healing process. A skin lesion which is unhealed after at least about one month, for example after at least about six months, can be categorised as chronic.

A chronic skin lesion is ulcerous where it involves focal loss of the epidermis and at least part of the dermis.

Malignant or pre-malignant chronic ulcerous skin lesions may arise in connection with a primary cancer of the skin, or with a metastasis to the skin from a local tumour or from a tumour in a distant site. They may be draining or non-draining. They may, for example, take the form of a cavity, an open area on the surface of the skin, skin nodules, or a nodular growth extending from the surface of the skin.

Benign chronic ulcerous skin lesions are not associated with cancer, and include venous leg ulcers, venous foot ulcers, arterial leg ulcers, arterial foot ulcers, decubitus ulcers (e.g. pressure sores, bedsores), post-surgical ulcerous lesions and chronic burn lesions. They may, for example, take the form of a cavity, an open area on the surface of the skin, skin nodules, or a nodular growth extending from the surface of the skin. Typically, they comprise an open granulating area on the surface of the skin.

Chronic ulcerous skin lesions are usually accompanied by other chronic symptoms apart from the failure of the normal healing process. Typical accompanying chronic symptoms include one or more of pain, exudation, malodour, excoriation, spreading of the wound, tissue necrosis, irritation and hyperkeratosis. Such symptoms can be extremely debilitating and embarrassing for patients, and can seriously harm the patient's quality of life. In severe cases, they can require amputation of limbs or even death.

Chronic ulcerous skin lesions can also be categorised according to their exudation. General categorisation is into the three categories "high exudation", "medium exudation" and "low exudation". Exudate management is a particularly difficult task for the caring professional attending to the patient. A balance needs to be struck between the desire to remove exudate to maintain the patient's quality of life at as high a level as possible, and maintenance of an appropriate level of fluid to prevent the lesion becoming too dry or too wet.

The Role of Inflammation and the Complement Cascade

The complement cascade during inflammation is part of the body's defence against invading microorganisms during the wound healing process. The complement cascade includes the formation of natural antimicrobials such as opsonins (C3b), chemotactic factors for neutrophils and mononuclear phagocytes (C5a) as well as anaphylatoxins (C5a, C3a).

The complement cascade is thus implicated with the general inflammation response in the underlying failure of chronic wounds to progress.

The kinin cascade leads to the production of bradykinin, which is implicated in the pain response.

Therefore, treatment of a patient to inhibit inflammation and/or the complement cascade and/or the kinin cascade, as well as other mechanisms involved in the early stages of wound healing, will be expected to assist in causing a chronic wound to start healing, and in preventing an acute wound from becoming chronic, and in the reduction of associated pain.

Prior Art Treatments

WO-A-00/07638, the contents of which are incorporated herein by reference, discloses bioadhesive hydrogel compositions and their use in wound dressings. The polymer composition is stated to preferably comprise also a non-hydrophilic (hydrophobic) polymer, and may comprise a specifically antimicrobial agent such as citric acid or stannous chloride. No information is given as to any effects of the hydrogel compositions on the proteases of wounds, for example human skin wounds. More generally, there is no teaching that the polymer per se in the hydrogel, including its associated water and ions, provides any inhibition of inflammation or the complement cascade alone or in combination with the additional beneficial effects on the wound mentioned as (1) to (5) above, without the need for other bioactive agents.

It is known to apply dressings to chronic skin lesions, with the aim of promoting their healing. Examples of such prior art dressings for chronic ulcerous skin lesions include Aquacel™ (ConvaTec) (http://www.dressings.org/Dressings/aquacel.html), Intrasite™ (Smith & Nephew) (http://www.dressings.org/Dressings/intrasit.gel.html) and Avance™ (Medlock Medical) (http://www.medlockmedical.com/woundcare/avance.htm).

Generally speaking, and without commenting specifically on the particular examples given above, prior art dressings for chronic ulcerous skin lesions suffer from a variety of problems. For example, they can cause maceration of peri-wound areas, they can absorb wound exudate only partially, they can cause contact dermatitis, varicose eczema or skin stripping (e.g. due to aggressive or allergenic adhesive materials). Furthermore, even in cases where the prior art dressings for chronic skin lesions contribute to successful healing, scarring of the healed wound and poor quality of healed tissue can often be found.

The prior art dressings for chronic ulcerous skin lesions can also be slow and difficult to apply and change, and require frequent changing. Many patients experience considerable—sometimes unbearable—pain associated with changing of the dressing, over and above the often considerable general pain associated with the lesion itself. The use of opiate painkillers to deal with this pain can lead to opiate dependency and addiction.

Prior art dressings that require frequent changing cause a significant increase in costs to healthcare services and providers, as a nurse or other healthcare professional needs to attend the patient correspondingly more often. In addition, the material costs of the dressings clearly are higher because of the frequent application of fresh dressings.

Specific anti-inflammatory chemical agents are well known. However, they are relatively expensive speciality chemicals and their addition to normal or normalising wounds can do more harm than good. In addition, they do not overcome the problem of pain and the other problems of the dressings themselves.

In an article entitled "A small study in healing rates and symptom control using a new sheet hydrogel dressing" in Journal of Wound Care, July 2004, 13(7), and in a poster presentation at the Tissue Viability Society (TVS) Conference in Torquay, UK, in April 2003, available on http://www.activahealthcare.co.uk/pdf/cs-actiformcool2.pdf, the contents of all of which are incorporated herein by reference, Sylvie Hampton described a study into the effects of a sheet hydrogel dressing on chronic leg and foot ulcers of at least six months duration (average 9months to two years) in 16 human patients. The pre-treatment ulcers of almost all of the patients were either high exudation or medium exudation. The sheet hydrogel dressing was supplied by Activa Healthcare of Burton-upon-Trent, UK (tel: +44 8450 606 707; web: www.activahealthcare.co.uk) under the name ActiFormCool™.

The results published by Sylvie Hampton showed the potential for substantial advantages deriving from the use of ActiFormCool™ as a dressing in the treatment of chronic leg and foot ulcers. However, neither the Journal of Wound Care article nor the poster presentation mentioned above disclosed the underlying nature of the therapeutic effect or the nature of any active component of the composition of ActiForm-Cool™. More generally, there was no teaching that the polymer per se in the hydrogel, including its associated water and ions, provides any specific or controlled interaction with proteins.

There is also no teaching that anionic polymers used for wound dressings need to combine both the correct balance of pendant anionic group with the appropriate counter cation in order to control interactions with proteins.

WO2007/007115, the contents of which are incorporated herein by reference, discloses the use of certain hydrogel compositions in the treatment of, inter alia, chronic ulcerous skin lesions. It discloses hydrogel compositions in the Examples derived from 2-acrylamido-2-methylpropane sulphonic acid (commonly known as NaAMPS) and, in some cases NaAMPS (as the major component) and the potassium salt of 2-acrylamido-2-methylpropane sulphonic acid (commonly known as SPAK) as the minor component).

WO 00/45864 discloses hydrogel bioadhesive compositions, which may be used in wound dressings. The hydrogel compositions may be formed from NaAMPS and SPAK. It states in this document that "where the ionic water soluble monomer comprises a mixture of NaAMPS and SPA or one of its salts, it is generally preferred that a high ratio of NaAMPS to SPA, for example 70:30 and above, is used".

BASIS OF THE PRESENT INVENTION

The present invention is based on our surprising finding that the hydrogels described below exhibit specific interactions with proteins, particularly fibrinogen. The hydrogel compositions have been found to be particularly suitable for use as wound dressings and/or for the inhibition of inflammation. Furthermore, we believe that, in use, the dressing is a self-regulating system, whereby the extent of inhibition of inflammation and/or the complement cascade and/or the kinin cascade can reduce as the wound approaches a normalised state, so that undesirable levels of inhibition of these responses are not found in practice. Furthermore, this self-regulation is exhibited by fresh dressings newly applied in dressing-changes, so that it appears that the hydrogel system responds sensitively to the state of healing of the wound.

It is believed that the hydrogels of the present invention may more closely mimic certain natural glycosminoglycans such as heparin than the hydrogels disclosed in PCT/GB2006/002632 (WO2007/007115). In particular, it is believed that they may more closely mimic the properties of heparin and other glycosaminoglycans that can lead to one or more of (i) improved wound healing, (ii) reduction in inflammation, (iii) inhibition of the complement cascade and (iv) inhibition of the kinin cascade.

BRIEF DESCRIPTION OF THE INVENTION

According to a first aspect, the present invention provides a hydrogel composition, preferably for the treatment of wounds, comprising a hydrophilic co-polymer carrying multiple pendant anionic groups, wherein the polymer is derived from a first monomer and a second monomer, wherein both monomers have an octanol:water partition coefficient LogP value of less than 0, and, the LogP value of the first monomer is greater (more positive) than the second monomer, preferably the difference between the LogP value for the two monomers is at least about 0.1, preferably at least about 0.2. The difference between the LogP value for the two monomers is preferably less than about 2. The first and second monomers may be any monomers suitable for producing a hydrogel composition, and include, but are not limited to the monomers disclosed herein. The pendant anionic groups may be sulphonyl groups, e.g. sulphonic acid groups or salts thereof.

The first monomer may have an octanol:water partition coefficient LogP value greater than the second monomer. Preferably, the weight ratio (w/w) of the first monomer/second monomer in the hydrogel composition is equal to or more than about 1.

Accordingly to a second aspect, the present invention provides a hydrogel composition, preferably for the treatment of wounds, comprising a hydrophilic copolymer formed from a first monomer and a second monomer, wherein the first monomer comprises an olefinically unsaturated sulphonic acid monomer or salt thereof, preferably an acrylic acid ester sulphonic acid monomer or salt thereof, and the second monomer comprises an olefinically unsaturated sulphonic acid monomer or salt thereof, different from the first monomer and preferably an acrylamide sulphonic acid monomer or salt thereof, the weight ratio (w/w) of the first monomer/second monomer in the hydrogel is equal to or more than about 1 and, either (i) the sulphonic group in both first and second monomers is in acidic form or (ii) the sulphonic group in both first and second monomers is in salt form and the counterion for both monomers is the same. The hydrophilic polymer in the second aspect preferably has multiple pendant anionic groups, preferably multiple pendant sulphonyl groups. Preferably, both monomers have an octanol:water partition coefficient LogP value less than 0, and the first monomer has a LogP value greater than (more positive than) than the second monomer.

Preferably, both first and second monomers are salts of olefinically unsaturated sulphonic acid monomers. Preferably, the counterion for both salts is the same, preferably sodium. Preferably, both first and second monomers have an octanol:water partition coefficient LogP value of less than 0, and the difference between LogP for the two monomers is at least about 0.1, preferably at least about 0.2. The difference between LogP between the two monomers is preferably less than about 1.

Reference to the "hydrogel composition of the present invention" herein shall be synonymous with "the hydrogel composition of the first aspect of the invention and/or the hydrogel composition of the second aspect of the invention".

The present invention further provides a method of treating a wound in a human or non-human mammal, particularly a human, comprising contacting the wound for an effective period of time with a hydrogel composition of the present invention.

The present invention further provides the use of a hydrogel composition of the present invention in the preparation of a topical medicament for the treatment of a wound, for example a chronic skin lesion, in a human or non-human mammal, particularly a human.

The hydrogel composition of the present invention may be for the treatment of a wound, for example a chronic skin lesion, in a human or non-human mammal, particularly a human.

The wound may be a skin wound. The wound may be a chronic ulcerous skin lesion. The chronic ulcerous skin lesion may be selected from venous leg ulcers, venous foot ulcers, arterial leg ulcers, arterial foot ulcers, decubitus ulcers (e.g. pressure sores, bedsores), post-surgical ulcerous lesions and chronic burn lesions.

The method of the present invention may comprise the contacting of the wound with the hydrogel composition of the present invention for an effective period of time to promote healing with simultaneous reduction in one or more of pain, exudation, malodour, excoriation, spreading of the wound, tissue necrosis, irritation and hyperkeratosis.

The present invention further provides a method of treating skin-derived or tissue-derived pain in a human or non-human mammal, particularly a human, by applying to the painful area as a topical dressing a hydrogel composition of the present invention.

The present invention further provides a method of inhibiting inflammation and/or the complement cascade and/or the kinin cascade in a human or non-human animal patient, comprising contacting an affected location of the patient's body for an effective period of time with a hydrogel composition of the present invention.

BRIEF DESCRIPTION OF THE FIGURES

FIGS. 1 to 3 show results from the Examples below, and in particular:

FIG. 1 shows the results of Table 1 below in a graph of retention time (mins) versus Log 10 molecular weight for various molecules in a gel permeation chromatography experiment detailed below;

FIG. 2 shows the results of Table 2 below in a graph of peak area (units) versus fibrinogen concentration (g/ml); and FIG. 3 shows the results from Table 6 below in a chart of fibrinogen concentration in supernatant fluid (g/100 ml) after 22 hrs exposure to six different hydrogels of Examples 1 to 6

Detailed Description of the Invention

According to a first aspect, the present invention provides a hydrogel composition, preferably for the treatment of wounds, comprising a hydrophilic co-polymer carrying multiple pendant anionic groups, wherein the polymer is derived from a first monomer and a second monomer, wherein both monomers have an octanol:water partition coefficient LogP value of less than 0, and the difference between the LogP value for the two monomers is at least about 0.1, preferably at least about 0.2. The difference between the LogP value for the two monomers is preferably less than about 2. The first and second monomers may be any monomers suitable for producing a hydrogel composition, and include, but are not limited to the monomers disclosed herein. The pendant anionic groups may be sulphonic acid groups or salts thereof.

The LogP value herein refers to the octanol:water partition coefficient, which is a measurement known to those skilled in the art. It represents the distribution of a substance (in this context, a monomer) between two immiscible solvents at equilibrium. LogP is the logarithm of the ratio of the mass concentration of the monomer in octanol divided by the mass concentration of the monomer in water at equilibrium (measured at 1 atm, 25° C. and pH 7).

LogP may be defined as follows:

$$\log P_{oct/wat} = \log_{10}([\text{monomer}]_{octanol}/[\text{monomer}]_{water}),$$

wherein $[\text{monomer}]_{octanol}$ is the mass concentration of the monomer in octanol at equilibrium and $[\text{monomer}]_{water}$ is the mass concentration of the monomer in water at equilibrium.

LogP is preferably measured using the shake flask method known to those skilled in the art. Further description of this method may be found in general textbooks and in the literature, such as in the review article by Leo et al in *Chem Rev* 71 (6): 525-616 (1971).

Preferably the pendant anionic groups are predominantly sulphonyl and are even more preferably combinations of structurally different sulphonyl groups. The structurally different pendant anionic groups may also be described by their relative hydrophilicity as exemplified by the calculated octanol:water partition coefficient (LogP).

Estimates for LogP values for chemicals can be found by using online calculation programs, including, but not limited to, www.molinspiration.com. Other methods may be used, such as the one described in *Perspectives in Drug Discovery and Design,* 19: 47-66, 2000. The more negative the value of Log P the greater the partitioning into water and hence the greater the hydrophilicity. For calculations performed on the monomers (calculated as the non ionised acid) on which the sulphonyl resides, the value of LogP for both monomers preferably is less than 0, for the more hydrophilic monomer the value is preferably less than about −1, more preferably less than about −1.5 even more preferably less than about −1.9. For the first, less hydrophilic monomer the value of Log P is greater than the second more hydrophilic monomer by preferably at least about 0.1, more preferably by about 0.2, but preferably less than a difference of about 2.0.

The first monomer may have a LogP value greater (more positive than) than the second monomer. Preferably, the weight ratio (w/w) of the first monomer/second monomer in the hydrogel composition is equal to or more than about 1, 1 more preferably about 1.5 or more, still more preferably about 2 or more, most preferably about 3 or more. The weight ratio (w/w) of the first monomer/second monomer in the hydrogel composition may be from 1 to 3 or may be from 1 to 2. The molar ratio of the first monomer/second monomer in the hydrogel composition may be equal to or more than about 1, 1 more preferably about 1.5 or more, still more preferably about 2 or more, most preferably about 3or more. The molar ratio of the first monomer/second monomer in the hydrogel composition may be from 1to 3or may be from 1 to 2.

Thus if the sulphonyl monomers are identified as the first and second sulphonyl monomers such that the first is the relatively less hydrophilic according to the Log P values and the second is the relatively more hydrophilic according to the Log P values, then it is preferred according to the present invention that the molar ratio of the first to the second sulphonyl monomers is between about 0:100 and about 100:1, preferably between about 1:100 and about 100:1, more preferably between about 1:90 and about 90:1, more preferably between about 1:80 to about 80:1, more preferably between about 1:50 and about 50:1, more preferably between about 1:25 and about 25:1, more preferably between about 1:10 and about 10:1, more preferably between about 1:5 and about 5:1, more preferably between about 1:3 and about 3:1 and even more preferably between about 1:3 and about 2:1. Accordingly to a second aspect, the present invention provides a hydrogel composition, preferably for the treatment of wounds, comprising a hydrophilic copolymer formed from a first monomer and a second monomer, wherein the first monomer comprises an olefinically unsaturated sulphonic acid monomer or salt thereof, preferably an acrylic acid ester sulphonic acid monomer or salt thereof, and the second monomer comprises an olefinically unsaturated sulphonic acid monomer or salt thereof, different from the first monomer and preferably an acrylamide sulphonic acid monomer or salt thereof, the weight ratio (w/w) of the first monomer/second monomer in the hydrogel is equal to or more than 1 and, either (i) the sulphonic group in both first and second monomers is in acidic form or (ii) the sulphonic group in both first and second monomers is in salt form and the counterion for both monomers is the same.

Preferably, the sulphonic group in both first and second monomers is in salt form and the counterion for both monomers is the same. Preferably, both first and second monomers are salts of olefinically unsaturated sulphonic acid monomers. Preferably, the counterion for both salts is the same, preferably sodium. Preferably, both first and second monomers have a LogP value of less than 0, and the difference between LogP for the two monomers is at least about 0.1, preferably at least about 0.2. The difference between LogP between the two monomers is preferably less than about 1.

Reference to the "hydrogel composition of the present invention" herein shall be synonymous with "the hydrogel composition of the first aspect of the invention and/or the hydrogel composition of the second aspect of the invention".

The first monomer preferably comprises a compound of formula (I)

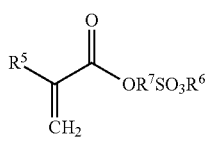

wherein $R5$ represents hydrogen or optionally substituted alkyl, preferably methyl or ethyl, $R6$ represents hydrogen or a cation and $R7$ represents an optionally substituted alkylene moiety, preferably of 1 to 4 carbon atoms. Preferably $R7$ represents optionally substituted n-propyl. Unless otherwise indicated, the term "alkyl", as used herein includes saturated monovalent hydrocarbon radicals having straight or branched moieties, preferably containing 1 to 4 carbons. Examples of alkyl groups include, but are not limited to, methyl, ethyl, propyl, isopropyl, and t-butyl. Unless otherwise indicated, the term "alkylene", as used herein, includes a divalent radical derived from straight-chain or branched alkane. Examples of alkylene radicals are methylene, ethylene (1,2-ethylene or 1,1-ethylene), propylene, trimethylene (1,3-propylene), tetramethylene (1,4-butylene), pentamethylene and hexamethylene.

$R1$, $R2$, $R3$, $R4$, $R5$ and $R7$ are optionally substituted by a group which preferably has a tendency to increase the water solubility of the compound. Suitable groups will be well known to a person of skill in the art. A preferred optional substituent is a hydroxyl, amino or ammonium group or a halogen (e.g. chlorine, bromine, or iodine) atom. A suitable cation is an alkali metal cation, especially sodium or potassium.

The second monomer preferably comprises a compound of formula (II)

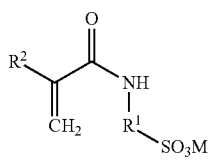

wherein $R1$ is an optionally substituted hydrocarbon moiety, $R2$ is hydrogen or optionally substituted methyl and ethyl, and M represents hydrogen or a cation.

$R1$ is preferably an optionally substituted alkylene, cycloalkylene or an aromatic moiety. Preferably $R1$ represents a saturated moiety or an aromatic moiety. $R1$ preferably contains from 3 to 12 carbon atoms, more preferably from 3 to 6 carbon atoms. A preferred moiety which $R1$ represents is

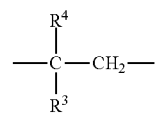

wherein $R3$ represents hydrogen or an optionally substituted straight or branched chain alkyl group possessing from 1 to 6 carbon atoms and $R4$ represents an optionally substituted straight or branched chain alkyl group possessing from 1 to 6 carbon atoms.

Most preferably, the first monomer comprises an acrylic acid (3-sulphopropyl) ester or a salt thereof, e.g. an alkali metal salt such as a sodium or potassium salt, of an analogue thereof. A particularly preferred example is acrylic acid (3-sulphopropyl) ester sodium salt, which may be termed NaSPA or SPANa (available in the form of a solid from Raschig).

Most preferably, the second monomer is 2-acrylamido-2-methylpropanesulphonic acid or a salt thereof, e.g. an alkali metal salt such as a sodium or potassium salt. A particularly preferred example is the sodium salt of 2-acrylamido-2-methylpropanesulphonic acid (available commercially at present from Lubrizol as a 58% aqueous solution).

Most preferably, the hydrogel composition comprises a copolymer of acrylic add (3-sulphopropyl) ester sodium salt (NaSPA) and the sodium salt of 2-acrylamido-2-methylpropanesulphonic acid (NaAMPS), in which the weight ratio of NaSPA/NaAMPS in the polymer is 1 or more, preferably 1.5 or more, more preferably 2 or more, still more preferably 3 or more.

Particular preferred examples of these respective monomers are the sodium salt of 2-acrylamido-2-methylpropanesulphonic acid, commonly known as NaAMPS, and acrylic acid (3-sulphopropyl) ester potassium salt, commonly known as SPA. NaAMPS is available commercially at present from Lubrizol as either a 50% aqueous solution (reference code LZ2405) or a 58% aqueous solution (reference code LZ2405A). SPA is available commercially in the form of a solid from Raschig The present invention further provides a method of treating a wound in a human or non-human mammal, particularly a human, comprising contacting the wound for an effective period of time with a hydrogel composition of the present invention.

The present invention further provides the use of a hydrogel composition of the present invention in the preparation of a topical medicament for the treatment of a wound, for example a chronic skin lesion, in a human or non-human mammal, particularly a human.

The hydrogel composition of the present invention may be for the treatment of a wound, for example a chronic skin lesion, in a human or non-human mammal, particularly a human.

The wound may be a skin wound. The wound may be a chronic ulcerous skin lesion. The chronic ulcerous skin lesion may be selected from venous leg ulcers, venous foot ulcers, arterial leg ulcers, arterial foot ulcers, decubitus ulcers (e.g. pressure sores, bedsores), post-surgical ulcerous lesions and chronic burn lesions.

The method of the present invention may comprise the contacting of the wound with the hydrogel composition of the present invention for an effective period of time to promote healing with simultaneous reduction in one or more of pain, exudation, malodour, excoriation, spreading of the wound, tissue necrosis, irritation and hyperkeratosis.

The present invention further provides a method of treating skin-derived or tissue-derived pain in a human or non-human mammal, particularly a human, by applying to the painful area as a topical dressing a hydrogel composition of the present invention.

The present invention further provides a method of inhibiting inflammation and/or the complement cascade and/or the kinin cascade in a human or non-human animal patient, comprising contacting an affected location of the patient's body for an effective period of time with a hydrogel composition of the present invention.

The method may be used to treat an inflammation of an inflamed part of a human or non-human animal in which a wound is not present, including, but not limited to, inflamed, unbroken skin. The method may be used to treat dermatitis and/or psoriasis.

Broadly speaking, the hydrogels for use in the present invention have multiple pendant sulphonyl groups, preferably multiple pendant structurally different sulphonyl groups and optionally also multiple pendant carboxylic groups and/or phosphonate groups, on each polymer molecule of the hydrogel.

By "pendant sulphonyl groups" we mean sulphonyl ($-SO_2-$) containing groups, most particularly sulpho ($-SO_2-OH$) groups in acid or salt form or organic groups which include sulpho ($-SO_2-OH$) groups in acid or salt form, which extend from the carbon atom containing chain ("carbon chain") of the polymer molecule and are covalently linked (pendant) to the carbon chain. Where the sulphonyl containing group is an organic group which includes the sulphonyl moiety, e.g. in a sulpho ($-SO_2-OH$) group in acid or salt form, the sulphonyl moiety is preferably located at or near the terminal free end of the organic group, i.e. the end distant from the carbon chain of the polymer molecule.

Some or all of the sulpho groups ($-SO_2-OH$) in acid or salt form may, if desired, be O-linked to the carbon chain of the polymer molecule, for example as organic sulphate groups. Some or all of the sulpho groups ($-SO_2-OH$) groups in acid or salt form may, if desired, be C-linked to the carbon chain of the polymer molecule, for example as organic sulphonate groups.

Where sulpho groups or some of them are present in salt form, the salt form may suitably be an alkali or alkaline earth or other multivalent (e.g. transition) metal or ammonium or organo-ammonium salt of the acid form ($-SO_2-OH$). For example, the salt form may be the sodium, potassium, lithium, caesium, calcium, magnesium, zinc or ammonium salt or combinations thereof. Preferably the salt form will comprise sodium ions, which may be in combination with one or more other salt forms such as, for example, potassium or ammonium. A combination of sodium and potassium counterions may be used. Most preferably, the counterions for first and second monomers are the same, most preferably sodium.

The organic sulphonyl containing groups or some of them may contain a carboxylate or carboxamido linkage unit. The polarity of these species, in conjunction with the sulphonyl groups, seems to play a part in achieving the desirable effects underlying the present invention. It is preferred that the carboxylate or carboxamido linkage unit, when present, is closer to the carbon chain of the polymer than the sulphonyl moiety.

By "pendant carboxylic groups" we mean carboxylate ($-CO_2-$) containing groups, most particularly carboxylic acid ($-CO_2H$) groups in acid or salt form or organic groups which include carboxylic acid ($-CO_2H$) groups in acid or salt form, which extend from the carbon atom containing chain ("carbon chain") of the polymer molecule and are covalently linked (pendant) to the carbon chain. Where the carboxylate containing group is an organic group which includes the carboxylate moiety, the carboxylate moiety is preferably located at or near the terminal free end of the organic group, i.e. the end distant from the carbon chain of the polymer molecule.

Where carboxylic acid groups or some of them are present in salt form, the salt form may suitably be an alkali or alkaline earth or other multivalent (e.g. transition) metal or ammonium or organo-ammonium salt of the acid form ($-CO_2H$). For example, the salt form may be the sodium, potassium, or ammonium salt or combinations thereof. Preferably the salt form will comprise sodium ions, in combination with one or more other salt forms such as, for example, potassium, or ammonium. A combination of sodium and potassium counterions can be particularly suitable. Where a combination of counterions is present in the hydrogel, any multivalent counterion (e.g. one or more of magnesium, zinc, calcium) is suitably present in a total molar proportion of up to about 5 mol % relative to the univalent (e.g. sodium) ions.

We have found that the hydrogels can be particularly effective when at least some of the sulphonyl and, if present, carboxylic, groups are present in salt form and the nature and/or relative number of associated countercations are selected as described in more detail below.

The finding, for the first time in these hydrogels, of an intrinsic controllable interaction with proteins considerably enhances the potential for the stimulation of wound healing and consequently makes effective treatment available to a wider class of patients having a range of wound conditions, including chronic ulcerous skin lesions and in particular chronic leg and foot ulcers that are refractory to prior art treatments. Patients who have adverse reactions to specific anti-inflammatory chemicals, or for whom the administration of specific anti-inflammatory agents might risk allergic reactions, side effects or other disadvantages, will now benefit from the present invention. The present invention assists in bringing the potential advantages of a novel anti-inflammatory treatment to the general public with reduced risk of adverse effects. In addition, since the hydrogels used in the present invention also have other beneficial effects as noted above, the dressings are potentially of great benefit to patients who have reactions to certain classes of antibiotics, painkillers or other bioactive agents conventionally used in, or in conjunction with, wound dressings, or who are addicted to or dependent on opiate or other powerful painkillers conventionally used in conjunction with wound care. Those people will be treatable using the present invention—in which the use of other bioactive agents such as specific anti-inflammatory agents, antibiotics or painkillers can be avoided—whereas previous treatment protocols were restricted by the need to avoid the problematic chemical agents such as anti-inflammatory agents, antibiotics, painkillers or other bioactive agents. Therefore, the novel findings constitute and make available a novel therapeutic application.

The composition of the present invention preferably absorbs one or more proteins, preferably fibrinogen. The composition of the present invention may initiate and/or promote clotting in a wound.

At least some of the pendant groups are preferably present in salt form, so that charge-balancing countercations other than H+ are present in the hydrogel associated with the pendant groups. The countercations may be selected from sodium, potassium, ammonium or organo-ammonium cations (primary ammonium, secondary ammonium, tertiary ammonium and quaternary ammonium cations). Two or more different countercations may be present in the hydrogel, and may be selected from sodium, potassium, ammonium or organo-ammonium cations (primary ammonium, secondary ammonium, tertiary ammonium and quaternary ammonium cations). Preferably, the countercation for the first and second monomers is the same.

Two or more different countercations associated with pendant anionic groups of the hydrogel, may be provided in a controlled relative molar proportion according to the extent of hydration of the countercations (i.e. according to the position of the countercations in the Hofmeister series of cations).

The polymers (including copolymers), both crosslinked and non-crosslinked, of the invention preferably comprise pendant anionic groups that are kosmotropic (water order makers) in nature. The cationic counterion is preferably chaotropic (disorder maker) or, at most, weakly kosmotropic. The polymers of the invention may contain a mixture of pendant anionic groups possessing different degrees of water order making e.g. varying in kosmotropic strength, for example comprising phosphate, phosphonate, sulphonyl, sulphate, sulphonate and carboxylate and combinations thereof. The extent of kosmotropic and chaotropic behaviour has been quantified by thermodynamic parameters such as the Jones Dole B viscosity coefficients. Preferred values of the Jones Dole B coefficient for the anion kosmotropic behaviour are greater than 0.1 and preferably greater than 0.2. Preferred values of the Jones Dole B coefficient for the cation chaotropic behaviour are greater than −0.1.

The polymers of the invention may thus contain a mixture of chaotropic and kosmotropic ions. The molar ratio of chaotropic to kosmotropic cation is preferably less than about 500:1, for example less than about 250:1, preferably less than about 200:1, for example less than about 100:1, for example less than about 80:1, for example less than about 50:1, and preferably more than about 2:1. For example, the ratio may be between about 2:1 and about 500:1, for example between about 5:1 and about 200:1, for example between about 5:1 and about 100:1, for example between about 7:1 and about 100:1, for example between about 10:1 and about 100:1.

The polymers of the invention may also comprise combinations of pendant anionic group differing in the extent of the kosmotropic behaviour. The molar ratio of pendant anionic kosmotropic groups with relatively larger Jones Dole B viscosity coefficients (higher kosmotropic behaviour) to pendant anionic kosmotropic groups with relatively smaller Jones Dole B viscosity coefficients (lower kosmotropic behaviour) is preferably between about 1000:1 and about 1:1000, more preferably between about 200:1 and about 1:200, and even more preferably between about 100:1 and about 1:100.

Thus, if the countercations are identified as the first and second countercations such that the first is the relatively more strongly hydrated according to the Hofmeister series of cations and the second is the relatively more weakly hydrated according to the Hofmeister series of cations, then it is preferred according to the present invention that when two or more countercations are present the molar ratio of the first to the second countercations in the hydrophilic polymer is less than about 500:1, preferably less than about 200:1, for example less than about 100:1, for example less than about 80:1, for example less than about 50:1, and preferably more than about 2:1. For example, the ratio may be between about 2:1 and about 500:1, for example between about 5:1 and about 200:1, for example between about 7:1 and about 100:1, for example between about 10:1 and about 100:1.

The first cation may, for example, be sodium and the second may, for example, be selected from potassium, primary ammonium, secondary ammonium, tertiary ammonium and quaternary ammonium, or the first may be potassium and the second may be selected from primary ammonium, secondary ammonium, tertiary ammonium and quaternary ammonium. The first cation is preferably sodium.

In one particular embodiment, the hydrophilic polymer is a copolymer comprising polymerised monomers carrying groups which provide the pendant anionic (e.g. sulphonyl) groups of the polymer. One or more additional monomers may optionally be present in the polymer if desired, provided that the ionic balance of the polymer mentioned above is maintained. At least some of the said pendant groups of the polymer are in salt form, preferably with a first countercation and a second countercation, different from the first. The said countercations are selected from relatively weakly hydrated cations according to the Hofmeister series of cations, for example sodium, potassium, primary ammonium, secondary ammonium, tertiary ammonium and quaternary ammonium cations. The countercations are preferably chosen such that the first is the relatively more strongly hydrated according to the Hofmeister series of cations and the second is the relatively more weakly hydrated according to the Hofmeister series of cations. For example, the first cation may be sodium and the second may be selected from potassium, primary ammonium, secondary ammonium, tertiary ammonium and quaternary ammonium, or the first may be potassium and the second may be selected from primary ammonium, secondary ammonium, tertiary ammonium and quaternary ammonium The molar ratio of the said first to the second countercations in the hydrophilic polymer is preferably less than about 500:1, preferably less than about 200:1, for example less than about 100:1, for example less than about 80:1, for example less than about 50:1, and preferably more than about 2:1. For example, the ratio may be between about 2:1 and about 500:1, for example between about 5:1 and about 200:1, for example between about 5:1 and about 100:1, for example between about 7:1 and about 100:1, for example between about 10:1 and about 100:1.

The polymer may suitably be formed by the polymerisation of monomers in which the groups which provide the pendant groups of the polymer are in salt form, such that the molar ratio of the monomer(s) in which the salt cation is the said first countercation in the hydrophilic polymer, to the monomer(s) in which the salt cation is the said second countercation in the hydrophilic polymer, is, correspondingly, preferably less than about 250:1, preferably less than about 200:1, for example less than about 100:1, for example less than about 80:1, for example less than about 50:1, and preferably more than about 2:1. For example, the ratio may be between about 2:1 and about 250:1, for example between about 5:1 and about 200:1, for example between about 5:1 and about 100:1, for example between about 7:1 and about 100:1, for example between about 10:1 and about 100:1. These ratios relate to univalent molar equivalents; in the case of multivalent cations associated with the (univalent) anionic groups of the monomer(s), the molar amounts of the monomer(s) will be correspondingly adjusted.

By the relevant choice of the type of sulphonate monomer and the choice of the countercation the interaction with proteins can be controlled as shown in the examples with the interaction with fibrinogen.

The hydrogel composition preferably comprises a polymer matrix holding a liquid (normally aqueous) phase retained within the hydrogel. The polymer matrix may for example be cross-linked or entangled, preferably cross-linked. The degree of cross-linking may be varied as desired. The polymeric matrix preferably consists of a cross-linked hydrophilic polymer. The liquid phase may, if desired, incorporate one or more other bioactive agents (e.g. particularly agents soluble or miscible in the liquid held within the polymer matrix of the hydrogel) to assist the healing process of the chronic skin lesion, or may be free or substantially free of such bioactive agents. It is a preferred feature of the present invention, however, that the hydrogel composition per se can be effective for the healing of wounds, the inhibition of inflammation and/or the complement cascade, without the need for other bioactive agents. Therefore, in one embodiment of the present invention the hydrogel composition is substantially or entirely free of added bioactive agents having specific therapeutic or other physiological activity.

The hydrogel composition is preferably used in sheet form. The hydrogel composition is preferably prepared in sheet form by polymerisation of a laid down layer of a liquid pre-gel mixture of polymerisable components, which are then cured to provide the polymerised mass. Preferably all or substantially all of the desired components of the hydrogel composition, including any water, are present in the pre-gel, and that no or substantially no drying or other adjustments are required after polymerisation (apart from minor conventional conditioning).

The contacting of the wound with the hydrogel composition comprising a hydrophilic polymer carrying multiple pendant sulphonyl groups, optionally with multiple pendant carboxylic groups, on each polymer molecule preferably takes place for a period of time or for a sequence of time periods to promote healing and/or the inhibition of inflammation and/or the complement cascade and/or the kinin cascade, preferably with simultaneous reduction in one or more of pain, exudation, malodour, excoriation, spreading of the wound, tissue necrosis, irritation and hyperkeratosis.

The effective amount of pendant sulphonyl groups, optionally with multiple pendant carboxylic groups, and the use of countercations for the salt forms thereof, including selection of the nature and/or molar ratio of any said two or more countercations present, for treating the wound, will vary from subject to subject.

The hydrophilic polymer used in the present invention may, if desired, comprise further multiple pendant anionic groups, in addition to the sulphonyl groups and optional carboxylic groups present. Where such additional anionic groups are present, they will typically be in relatively small numbers in comparison with the sulphonyl and optional carboxylic groups. Any such additional anionic groups may be present in acid or salt form, provided that the ionic balance of the polymer mentioned herein is maintained. Examples of such additional pendant anionic groups that may be present are relatively strongly hydrated anions according to the Hofmeister series of anions, for example phosphate or phosphonyl groups.

A wound to be treated using any of the aspects of the present invention may be of any type, acute or chronic. The wound may for example be a chronic ulcerous skin lesion, for example a malignant or pre-malignant chronic ulcerous skin lesion or a benign chronic ulcerous skin lesion.

The chronic ulcerous skin lesion may be a high exudation lesion, a medium exudation lesion or a low exudation lesion.

The hydrogel composition has the capacity to absorb many times (e.g. at least about 2.5 times, for example at least about 5 times, for example at least about 10 times, for example between about 10 and about 50 times) its own weight of exudate or other fluid in 24 hours. Therefore, the exudate management capacity of the composition can be selected according to the intended target patients and lesions for treatment. The hydrogel preferably has a water activity greater than about 0.4, for example greater than about 0.5, for example greater than about 0.6, for example greater than about 0.7, preferably greater than about 0.8, preferably greater than about 0.9, preferably greater than about 0.95, preferably greater than about 0.97 but less than about 0.99 in the absence of maceration. In the presence of maceration the hydrogel preferably has a water activity less than about 0.95, more preferably less than about 0.9. As mentioned below, in some instances the water activity of the hydrogel may be substantially lower than about 0.4. As described in more detail below, one particularly suitable hydrogel for use in the present invention may have a water activity in the range of about 0.6 to about 0.89.

As discussed in more detail below, the beneficial effects of the hydrogel according to the present invention are believed to derive from the presence of at least two or more structurally different sulphonyl monomers, optionally with multiple pendant carboxylic groups, of the polymer molecules and the choice of the relevant counter cations. It is believed that these act in situ at the zone of contact with the wound to interact more specifically than hither to possible with proteins that lead to inhibit inflammation and/or the complement cascade, optionally with other effects such as selectively concentrating one or more naturally exuded salts in the ulcerous region of the lesion (the "wound bed") and/or selectively absorbing one or more naturally exuded salts in the wound bed (see WO2007/007115). The hydrogel thus acts without the need for externally applied salt or other ionic aqueous solutions, and preferably also in the absence of salt or other ionic aqueous solutions in the liquid held within the polymer matrix of the hydrogel, so that the blocking mechanism preventing completion of the normal wound healing process is overridden, bypassed, shut off or otherwise disabled, and continuation of the normal wound healing process to substantial completion is enabled or initiated.

The selectivity of the anti-inflammatory effect is preferably achieved through the control of the counterion(s), if any, present on the sulphonyl groups or present on the multiple sulphonyl and carboxylic groups and the nature of the sulphonyl group. Generally speaking, it is believed that selection of, say, sodium counterions on —SO3- groups (i.e. a sulpho group in salt form) will favour concentration of sodium salts (e.g. sodium chloride) in the wound bed, whereas selection of, say, potassium counterions on —SO3- groups will favour concentration of potassium salts (e.g. potassium chloride) in the wound bed whereas selection of, say, calcium counterions on —SO3- groups will favour concentration of calcium salts (e.g. calcium chloride) in the wound bed. For example, we believe that it will be advantageous for the molar ratio of sodium ions to potassium ions associated in the hydrogel composition (or sodium ions to other more weakly hydrated cations according to the Hofmeister series of cations) to be less than about 500:1, preferably less than about 200:1, for example less than about 100:1, for example less than about 80:1, for example less than about 50:1, and preferably more than about 2:1, for example, between about 2:1 and about 500:1, for example between about 5:1 and about 200:1, for example between about 5:1 and about 100:1, for example between about 7:1 and about 100:1, for example between about 10:1 and about 100:1. Other counterions may also be used, as discussed above, in which case the molar ratios stated above apply instead to first and second cations in place of sodium and potassium ions, the first being the relatively more strongly hydrated according to the Hofmeister series of cations and the second being the relatively more weakly hydrated according to the Hofmeister series of cations.

From this, it is now possible to control the healing process in wounds, for example in chronic ulcerous skin lesions, for the first time, without the need for externally applied salts or other bioactive agents apart from the dressing itself, and more particularly without the need for salts or other bioactive agents in the dressing apart from the hydrogel polymer matrix (including the associated water and the ions of the hydrogel polymer) of the dressing itself.

The Hydrogel, Dressing and Treatment

The expression "hydrogel" and like expressions, used herein, are not to be considered as limited to gels which contain water, but extend generally to all hydrophilic gels, including those containing organic non-polymeric components in the absence of water. The gel forming agent may, for example, be selected from natural hydrophilic polymers, synthetic hydrophilic polymers, gelling hydrophilic biopolymers and all combinations thereof. The term "hydrogel" is used herein regardless of the state of hydration, and therefore includes, for example, hydrogels that are in a dehydrated or anhydrous state or in a state of partial hydration.

Hydrogels are described in greater detail in Hydrogels, Kirk-Othmer Encyclopedia of Chemical Technology, 4th Edition, vol. 7, pp. 783-807, John Wiley and Sons, New York, the contents of which are incorporated herein by reference.

The expression "polymer" and like expressions, used herein, includes homopolymers, copolymers and all mixtures and combinations thereof. The expression "polymer" and like expressions, used herein, includes cross-linked and uncrosslinked polymers, as well as polymers characterised by entangled polymer chains. The expression "polymer" and like expressions, used herein, includes bicontinuous and higher multicontinuous intermeshing polymer systems, in which two or more polymers form identifiable intermeshing phases extending within the hydrogel mass.

Hydrogels are, generally speaking, hydrophilic polymers characterized by their hydrophilicity (i.e. capacity to absorb large amounts of fluid such as wound exudate) and insolubility in water: i.e. they are capable of swelling in water while generally preserving their shape.

The hydrophilicity is generally due to groups such as hydroxyl, carboxy, carboxamido, sulphonate and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of crosslinking, but may result from electrostatic, hydrophobic or dipole-dipole interactions.

The hydrogels in the present invention include as a necessary component a hydrophilic polymer carrying multiple pendant sulphonyl groups on each polymer molecule, preferably in salt form counterbalanced by one or more cations.

Generally, the degree of sulphonylation of such a polymer is on average (number average) at least about one pendant sulphonyl group per linear 30 carbon atoms of the carbon atom backbone of the polymer, at least about one pendant sulphonyl group per linear 12 carbon atoms of the carbon atom backbone of the polymer, for example at least about one pendant sulphonyl group per linear six carbon atoms of the carbon atom backbone of the polymer. More preferably, the polymer will contain on average at least about two pendant sulphonyl groups per linear six carbon atoms of the carbon atom backbone of the polymer, for example up to about three pendant sulphonyl groups per linear six carbon atoms of the carbon atom backbone of the polymer. At the higher levels of sulphonylation it is preferred that pendant carboxylate groups will be substantially absent.

Most preferably, the polymer contains one pendant sulphonyl group per linear two carbon atoms of the carbon atom backbone of the polymer. Such a polymer is readily prepared by polymerising (meth)acrylic acid derivatives such as esters or amides using monomers containing one sulphonyl group per molecule. The sulphonyl groups may be present in acid, ester, salt or other suitable form, and may be covalently linked to the carbon atom backbone of the polymer. A suitable sulphonyl moiety is the —$SO_3$- species, either in acid form (—$SO_3H$) or in salt form (—$SO_3M$, where M is a univalent metal counterion, or —$SO_3MO_3S$— where M is a divalent metal counterion), or the organic sulphate species (for example, —O—$SO_3H$ in acid form, or in corresponding salt form). Suitable linking moieties include alkylene bridges, alkylene-ester bridges, —O— bridges and alkylene-amide bridges. The alkylene moieties may be straight or branched, saturated and preferably contain from 1 to about 8 carbon atoms.

Such hydrophilic polymers include, for example, polymers derived from (meth)acryloyloxyalkylsulphonates, polymers of sulpho-substituted acrylamides such as acrylamidoalkanesulphonic acids, polymers of salts of any of the foregoing (for example, alkali or alkaline earth metal salts or ammonium or quaternary organ-ammonium salts), or any combination thereof. Mixtures of such polymers with each other are also envisaged.

Such polymers may, if desired, be used together with sulpho-free polymers. Such other polymers, if present, may suitably be selected from homopolymers or copolymers of acrylic and methacrylic acid esters, including hydroxyalkyl (meth)acrylates, 2-(N,N-dimethylamino)ethyl methacrylate, polymers and copolymers of other substituted and unsubstituted acrylamides, polymers and copolymers of N-vinylpyrrolidinone, and polyelectrolyte complexes.

The hydrophilic polymer carrying multiple pendant sulphonyl groups, optionally with multiple pendant carboxylic groups, on each polymer molecule should be present at least at the lesion-contacting surface of the hydrogel composition. If desired, the hydrophilic polymer carrying multiple pendant sulphonyl groups, optionally with multiple pendant carboxylic groups, on each polymer molecule may also be present in the internal bulk of the composition, and/or a sulphonyl-free polymer or combination of polymers may be present in the internal bulk of the composition.

Generally, the degree of carboxylation of such a polymer is on average (number average) at least about one pendant carboxylic group per linear 100 carbon atoms of the carbon atom backbone of the polymer, for example up to about one pendant carboxylic group per linear six carbon atoms of the carbon atom backbone of the polymer.

The hydrogel used in the present invention suitably comprises a substantially water-insoluble, slightly crosslinked, partially neutralized, gel-forming polymer material having the pendant sulphonyl groups, and optionally pendant carboxylic groups, in acid or salt form at least at its lesion-contacting surface. Such polymer materials can be prepared from polymerizable, unsaturated, acid- and ester-containing monomers. Any polymer to be present at the lesion-contacting surface of the composition will contain pendant sulphonyl groups, for example —$SO_3$- in acid or salt form, and optionally carboxylic groups in acid or salt form, as described herein. Thus, such monomers include the olefinically unsaturated acids, esters and anhydrides which contain at least one carbon to carbon olefinic double bond. More specifically, these monomers can be selected from olefinically unsaturated carboxylic acids, carboxylic esters, carboxylic acid anhydrides; olefinically unsaturated sulphonic acids; and mixtures thereof.

Olefinically unsaturated carboxylic acid, carboxylic acid ester and carboxylic acid anhydride monomers include the acrylic acids typified by acrylic acid itself, methacrylic acid, ethacrylic acid, α-chloroacrylic acid, α-cyano-acrylic acid, β-methyl-acrylic acid (crotonic acid), α-phenyl acrylic acid, β-acryloxy-propionic acid, sorbic acid, α-chloro-sorbic acid, angelic acid, cinnamic acid, p-chloro-cinnamic acid, β-styryl-acrylic acid (1-carboxy-4-phenyl-1,3-butadiene), itaconic acid, citraconic acid, mesaconic acid, glutaconic acid, aconitic acid, maleic acid, fumaric acid, tricarboxyethylene and maleic acid anhydride and salts (e.g. alkali metal salts such as sodium, potassium and lithium salts) thereof. For forming any polymer to be present at the lesion-contacting surface of the composition, the monomer or monomer mixture will include a monomer containing pendant sulphonyl groups, e.g. —SO3- in salt form counter balanced by sodium and or potassium and ammonium cations.

Olefinically unsaturated sulphonic acid monomers include aliphatic or aromatic vinyl sulphonic acids such as vinylsulphonic acid, allylsulphonic acid, vinyltoluenesulphonic acid and styrene sulphonic acid; vinyl sulphobetaines such as SPDA (1-propanaminium N,N-dimethyl-N-[2-[(1-oxo-2-propenyl)oxy]-3-sulfo hydroxide, inner salt (available from Raschig); acrylic and methacrylic sulphonic acid such as sulphoethyl acrylate, sulphoethyl methacrylate, sulphopropyl acrylate, sulphopropyl methacrylate, 2-hydroxy-3-acryloxy propyl sulphonic acid, 2-hydroxy-3-methacryloxy propyl sulphonic acid and 2-acrylamido-2-methyl-propanesulphonic acid and salts (e.g. ammonium or alkali metal salts, such as sodium, potassium and lithium salts, or alkaline earth metal salts, such as calcium or magnesium) thereof.

The monomers may suitably be used in admixture with each other or with other monomers. In one particularly useful embodiment of the invention, a monomer which has a first countercation associated with it may be used in admixture with one or more monomer which has/have one or more second/further countercation(s) associated with it/them, and preferably the first countercation is the same as the second countercation. The monomers in their anionic form (i.e. disregarding the counter-cation) may be the same or different. In this way, the proportions of different cations (e.g. alkali metal ions such as sodium or potassium, or primary, secondary, tertiary or quaternary ammonium ions) can be finely controlled in the resultant polymer (homopolymer or copolymer), as previously discussed. The particular weight ratios of one monomer to the or each other monomer, and/or the respective countercations, can be selected within wide limits by those skilled in the art, depending on the desired properties of the resultant hydrogel polymer, and examples of suitable molar ratios have been given above in the Further examples of suitable monomers for use in the present invention include: a polyalkylene glycol acrylate or a substituted derivative thereof; a polyalkylene glycol methacrylate or a substituted derivative thereof; acrylic acid and salts thereof (e.g. alkali metal salts such as sodium, potassium and lithium salts); 2-acrylamido-2-methyl-propanesulphonic acid and salts thereof (e.g. ammonium or alkali metal salts, such as sodium, potassium and lithium salts, or alkaline earth metal salts, such as calcium or magnesium); acrylic acid (3-sulphopropyl) ester or a substituted derivative thereof or a salt thereof (e.g. an alkali metal salt such as sodium, potassium or lithium salt); diacetone acrylamide (N-1,1-dimethyl-3-oxobutyl-acrylamide); a vinyl lactam (e.g. N-vinyl pyrrolidone or a substituted derivative thereof); an optionally substituted N-alkylated acrylamide such as hydroxyethyl acrylamide; and an optionally substituted N,N-dialkylated acrylamide; and/or N-acryloyl morpholine or a substituted derivative thereof. For forming any polymer to be present at the lesion-contacting surface of the composition, the monomer or monomer mixture will include a monomer containing pendant sulphonyl groups, e.g. —SO3- in acid or salt form, and optionally carboxylic groups in acid or salt form.

The above monomers and monomer types may optionally include substituent groups. Optional substituents of the monomers used to prepare the hydrogels used in the present invention may preferably to selected from substituents which are known in the art or are reasonably expected to provide polymerisable monomers which form hydrogel polymers having the properties necessary for the present invention. Suitable substituents include, for example, lower alkyl, hydroxy, halo and amino groups.

In one particular form of the present invention, the hydrogel material may be free of uncrosslinked polymerised styrene sulphonates. In another particular form of the present invention, the hydrogel material may be free of any styrene sulphonate component, whether polymerised or unpolymerised and whether crosslinked or uncrosslinked.

The hydrogel used in the present invention preferably comprises a plasticised three-dimensional matrix of cross-linked polymer molecules, and preferably has sufficient structural integrity to be self-supporting even at very high levels of internal water content, with sufficient flexibility to conform to the surface contours of mammalian, preferably human, skin or other surface with which it is in contact.

The hydrogel generally comprises, in addition to the cross-linked polymeric network, an aqueous or non-aqueous plasticising medium including an organic plasticiser. This plasticising medium is preferably present in the same precursor solution as the monomer(s). The plasticising medium may comprise additional ingredients in solution or dispersion, as described in more detail below.

The hydrogel composition may suitably be present as a thin sheet, preferably supported by a sheet support member to provide mechanical strength. The sheet support member for the hydrogel may, for example, be a thin scrim or net structure, for example formed of a synthetic and/or natural polymer such as polyethylene or polypropylene. The sheet support member for the hydrogel may overlie the hydrogel sheet on the major face of the sheet directed away from the lesion in use, or may be embedded within the hydrogel polymer. The sheet support member may, if desired, extend beyond the margins of the hydrogel composition, and may be provided with a skin adhesive portion to secure the dressing to the skin. The skin adhesive portion may be hydrogel in nature (for example a plasticised tacky hydrogel, which may be the same as or different from the hydrogel provided on the support member for the treatment according to the present invention), or may be another type of skin adhesive selected from the many skin adhesives known in the wound dressings art. The support member may be or may comprise a sheet member as defined in WO 2007/113452, the contents of which is incorporated herein by reference. In particular, the support member may comprise or be a "fibrous absorbent sheet member" as defined in WO 2007/113452 and/or may comprise one or more other sheet members defined as "other absorbent sheet members" in WO 2007/113452. The dressing of the present invention may comprise an optional "net member" as defined in WO 2007/113452.

The hydrogel sheet may be part of a multi-layer composite, including further layers such as further hydrogels and/or other polymers and/or other sheet support members. For example, a breathable (air and/or moisture permeable) polymeric film (e.g. of polyurethane) may overlie the hydrogel sheet or composite on the major face of the sheet or composite directed away from the lesion in use.

The hydrogel composition and other sheet components as desired may preferably be provided with a release layer (e.g. of non-stick paper or plastic, such as siliconised paper or plastic) to protect one or both major face of the sheet prior to use.

The hydrogel composition and other sheet components as desired can constitute a dressing for the chronic ulcerous skin lesion which can, after removal of any release layer as appropriate, be applied to the lesion directly so that the major face which presents at its surface the hydrogel carrying pendant sulphonyl groups is directed towards the lesion and contacts the lesion, preferably the wound bed and surrounding tissues.

If desired, conventional bandages, cloths or other protective fabrics or materials can subsequently be applied to encase the dressing and hold it in place on the lesion.

Particularly where the hydrogel is plasticised, there is very slight adhesion between the hydrogel dressing and the patient's skin or the lesion tissue. This has the beneficial effect that one nurse or other healthcare professional can apply the dressing and can then prepare any desired bandages, cloths or the like for subsequent application. The dressing of the present invention will remain in place because of the mild adhesion, even if the patient moves before the further bandages etc. are applied.

The precursor liquid can comprise a solution of the gel-forming polymer in a relatively volatile solvent, whereby the hydrogel is deposited as a residue on evaporation of the solvent, or—more preferably—the precursor liquid will comprise a solution of the monomer(s), cross-linking agent, plasticiser, and optionally water and other ingredients as desired, whereby the hydrogel is formed by a curing reaction performed on the precursor liquid after application to the substrate to which the hydrogel is to be applied.

Preparation of the Hydrogel and Dressing

In the following discussion, the second form of precursor solution and application protocol (in situ polymerisation of the hydrogel) will be discussed. The solvent deposition method carried out on a pre-formed gel-forming polymer is well known and the details of that procedure do not need to be reproduced here.

The polymerisation reaction is preferably a free-radical polymerisation with cross-linking, which may for example be induced by light, heat, radiation (e.g. ionising radiation), or redox catalysts, as is well known.

For example, the free radical polymerisation may be initiated in known manner by light (photoinitiation), particularly ultraviolet light (UV photoinitiation); heat (thermal initiation); electron beam (e-beam initiation); ionising radiation, particularly gamma radiation (gamma initiation); non-ionising radiation, particularly microwave radiation (microwave initiation); or any combination thereof. The precursor solution may include appropriate substances (initiators), at appropriate levels, e.g. up to about 5% by weight, more particularly between about 0.002% and about 2% by weight, which serve to assist the polymerisation and its initiation, in generally known manner.

Preferred photoinitiators include any of the following either alone or in combination:

Type I-α-hydroxy-ketones and benzilidimethyl-ketals e.g. Irgacure 651 (2,2-dimethoxy-2-phenylacetophenone). These are believed on irradiation to form benzoyl radicals that initiate polymerisation. Photoinitiators of this type that are preferred are those that do not carry substituents in the para position of the aromatic ring.

Preferred photoinitiators are 1-hydroxycyclohexyl phenyl ketone, for example as marketed under the trade name Irgacure 184 by Ciba Speciality Chemicals; Irgacure 651 (2,2-dimethoxy-2-phenylacetophenone); Darocur 1173 (2-hydroxy-2-propyl phenyl ketone); and mixtures of Irgacure 184 and Darocur 1173.

Photo-polymerisation is particularly suitable, and may be achieved using light, optionally together with other initiators, such as heat and/or ionising radiation. Photoinitiation will usually be applied by subjecting the pre-gel reaction mixture containing an appropriate photoinitiation agent to ultraviolet (UV) light. The incident UV intensity, at a wavelength in the range from 240 to 420 nm, is typically greater than about 10 mW/cm2. The processing will generally be carried out in a controlled manner involving a precise predetermined sequence of mixing and thermal treatment or history.

The UV irradiation time scale should ideally be less than 60 seconds, and preferably less than 10 seconds to form a gel with better than 95% conversion of the monomers. Those skilled in the art will appreciate that the extent of irradiation will be dependent on a number of factors, including the UV intensity, the type of UV source used, the photoinitiator quantum yield, the amount of monomer(s) present, the nature of the monomer(s) present and the presence of polymerisation inhibitor.

The precursor solution (pre-gel) containing the monomer(s) and preferably cross-linking agent, water, plasticiser, photoinitiator and optionally other components as described below, is initially laid down on a substrate. Where the hydrogel composition is to be prepared in sheet for, the substrate will be a sheet. It may suitably comprise a release layer and any desired sheet support member that may be interposed between the release layer and the hydrogel composition, or embedded within the hydrogel composition, in the finished dressing. In this way, the precursor solution can be polymerised is situ on the release layer, preferably with all or substantially all other components of the final dressing in place.

In one preferred embodiment, (on the one hand) the precursor solution in contact with the substrate to which it is to be applied and (on the other hand) the source of the polymerisation initiator (e.g. the radiation source) may move relative to one another for the polymerisation step. In this way, a relatively large amount of polymerisable material can be polymerised in one procedure, more than could be handled in a static system. This moving, or continuous, production system is preferred.

After completion of the polymerisation, the product is preferably sterilised in conventional manner. The sterile composite may be used immediately, e.g. to provide a skin-adhesive layer in an article, or a top release layer may be applied to the composite for storage and transportation of the composite.

If desired, certain ingredients of the hydrogel may be added after the polymerisation and optional cross-linking reaction. However, it is generally preferred that substantially all of the final ingredients of the hydrogel are present in the precursor solution, and that—apart from minor conventional conditioning or, in some cases, subsequent modifications caused by the sterilisation procedure—substantially no chemical modification of the hydrogel takes place after completion of the polymerisation reaction.

Monomers

The monomers are discussed in more detail above. Particularly preferred monomers include: the sodium salt of 2-acrylamido-2-methylpropane sulphonic acid, commonly known as NaAMPS, which is available commercially at present from Lubrizol as either a 50% aqueous solution (reference code LZ2405) or a 58% aqueous solution (reference code LZ2405A); the potassium salt of 2-acrylamido-2-methylpropane sulphonic acid (Potassium AMPS), which is available commercially at present from Lubrizol; the ammonium salt of 2-acrylamido-2-methylpropane sulphonic acid (Ammonium AMPS), which is available commercially at present from Lubrizol; acrylic acid (3-sulphopropyl) ester potassium salt, commonly known as SPA or SPAK (SPA or SPAK is available commercially in the form of a pure solid from Raschig); acrylic acid (3-sulphopropyl) ester sodium salt, commonly known as SPANa (SPANa is available commercially in the form of a pure solid from Raschig); and SPDA. Acrylic acid (BASF) may be used as supplied or in partial or complete salt form where the salt counterion is an alkali metal (e.g. sodium or potassium), alkaline earth metal (e.g. calcium) or ammonium. Mixtures of any two or more of the above monomers may be used. When a mixture of the monomers is used, it may, for example, be a mixture of NaAMPS and SPAK, a mixture of NaAMPS and SPANa, a mixture of NaAMPS and Potassium AMPS, a mixture of NaAMPS and Ammonium AMPS, or a mixture of NaAMPS and acrylic acid. The relative amounts of the monomers in a mixture will be dictated by the desired ratio of counterions (e.g. potassium, sodium and ammonium) in the hydrogel, as well as the required properties of the copolymer, and may be selected easily by those skilled in the art, if necessary with routine testing of the copolymers prepared.

Cross-Linking Agents

Conventional cross-linking agents are suitably used to provide the necessary mechanical stability and to control the adhesive properties of the hydrogel. The amount of cross-linking agent required will be readily apparent to those skilled in the art such as from about 0.01% to about 0.5%, particularly from about 0.05% to about 0.4%, most particularly from about 0.08% to about 0.3%, by weight of the total polymerisation reaction mixture. Typical cross-linkers include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide.

Organic Plasticisers

The one or more organic plasticiser, when present, may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticiser. An alternative preferred plasticiser is the ester derived from boric acid and glycerol. When present, the organic plasticiser may comprise up to about 45% by weight of the hydrogel composition.

Surfactants

Any compatible surfactant may optionally be used as an additional ingredient of the hydrogel composition. Surfactants can lower the surface tension of the mixture before polymerisation and thus aid processing. The surfactant or surfactants may be non-ionic, anionic, zwitterionic or cationic, alone or in any mixture or combination. The surfactant may itself be reactive, i.e. capable of participating in the hydrogel-forming reaction. The total amount of surfactant, if present, is suitably up to about 10% by weight of the hydrogel composition, preferably from about 0.05% to about 4% by weight.

The surfactant may, for example, comprise at least one propylene oxide/ethylene oxide block copolymer, for example such as that supplied by BASF Plc under the trade name Pluronic P65 or L64.

Other Additives

The hydrogel in the composite of the present invention may include one or more additional ingredients, which may be added to the pre-polymerisation mixture or the polymerised product, at the choice of the skilled worker. Such additional ingredients are selected from additives known in the art, including, for example, water, organic plasticisers, surfactants, polymeric material (hydrophobic or hydrophilic in nature, including proteins, enzymes, naturally occurring polymers and gums), synthetic polymers with and without pendant carboxylic acids, electrolytes, osmolites, pH regulators, colorants, chloride sources, bioactive compounds and mixtures thereof. The polymers can be natural polymers (e.g. xanthan gum), synthetic polymers (e.g. polyoxypropylene-polyoxyethylene block copolymer or poly-(methyl vinyl ether alt maleic anhydride)), or any combination thereof. By "bioactive compounds" we mean any compound or mixture included within the hydrogel for some effect it has on living systems, whether the living system be bacteria or other microorganisms or higher animals such as the patient. Bioactive compounds that may be mentioned include, for example, pharmaceutically active compounds, antimicrobial agents, antiseptic agents, antibiotics and any combination thereof. Antimicrobial agents may, for example, include: sources of oxygen and/or iodine (e.g. hydrogen peroxide or a source thereof and/or an iodide salt such as potassium iodide) (see, for example Bioxzyme™ technology, for example in The Sunday Telegraph (UK) 26 Jan. 2003 or the discussion of the Oxyzyme™ system at www.wounds-uk.com/posterabstracts2003.pdf); honey (e.g. active Manuka honey); antimicrobial metals, metal ions and salts, such as, for example, silver-containing antimicrobial agents (e.g. colloidal silver, silver oxide, silver nitrate, silver thiosulphate, silver sulphadiazine, or any combination thereof), hyperchlorous acid; or any combination thereof.

In the Bioxzyme system, a dressing comprises two hydrogels. One contains glucose based antibacterial compounds and the other contains enzymes that convert the glucose into hydrogen peroxide. When these are exposed to air and contacted together at a wound site, the enzyme-containing gel being adjacent the skin and the glucose-containing gel overlying the enzyme-containing gel, a low level steady flow of hydrogen peroxide is produced, which inhibits anaerobic bacteria. This antibacterial effect can be enhanced by the inclusion of a very low level of iodide (less than about 0.04%) in the hydrogel. The hydrogen peroxide and the iodide react to produce iodine, a potent antimicrobial agent.

Hydrogels incorporating antimicrobial agents may, for example, be active against such organisms as *Staphylococcus aureus* and *Pseudomonas aeruginosa*.

Agents for stimulating the healing of wounds and/or for restricting or preventing scarring may be incorporated into the hydrogel. Examples of such agents include growth factors such as TGF (transforming growth factor), PDGF (platelet derived growth factor), KGF (keratinocyte growth factor, e.g.

KGF-1 or KGF-2), VEGF (vascular endothelial growth factor), IGF (insulin growth factor, optionally in association with one or more of IGF binding protein and vitronectin), e.g. from GroPep Ltd, Australia or Procyte, USA (see, e.g. WO-A-96/02270, the contents of which are incorporated herein by reference); cell nutrients (see, e.g., WO-A-93/04691, the contents of which are incorporated herein by reference); glucose (see, e.g., WO-A-93/10795, the contents of which are incorporated herein by reference); an anabolic hormone or hormone mixture such as insulin, triiodothyronine, thyroxine or any combination thereof (see, e.g., WO-A-93/04691, the contents of which are incorporated herein by reference); or any combination thereof.

Additional polymer(s), typically rheology modifying polymer(s), may be incorporated into the polymerisation reaction mixture at levels typically up to about 10% by weight of total polymerisation reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

Additional osmolite(s) may be included to modify the osmolarity of the hydrogel. Osmolites may be ionic (e.g. electrolytes, for example salts which are readily soluble in the aqueous phase of the hydrogel to increase the ionic strength of selected cations or anions and hence the osmolarity of the hydrogel). By selecting the ions present in an ionic osmolite, and particularly by selecting the cation so as to correspond or not with cationic counterions in the monomer(s) of the hydrogel, the ionic strength of certain anions (e.g. chloride) can be varied with fine control, without substantially changing the ionic strength of cations already present in very large amounts as counterions of the monomer(s).

Osmolites may be organic (non-ionic), for example organic molecules which dissolve in or intimately mix with the aqueous phase of the hydrogel to increase the osmolarity of the hydrogel deriving from non-ionic species in the aqueous phase. Such organic osmolites include, for example, water-soluble sugars (e.g. glucose and other monosaccharides), polyhydric alcohols (e.g. glycerol and other polyhydroxylated alkanols).

Additive ingredients may serve more than one purpose. For example, glycerol may serve as an organic plasticiser and an osmolite.

The hydrogel may comprise one or more complexing or chelating agents, which may include, but are not limited to, organic poly-carboxylic acids, and includes, but is not limited to, agents that can form complexes with or chelate to one or more metal ions. The complexing agent may be selected from di-, tri- and tetra-carboxylic acids. Preferably, the one or more complexing or chelating agents contain a moiety in which two carboxylic acid groups ($CO_2H$) or salts thereof are separated by three or four covalent bonds (e.g. three bonds in malic acid: $(HO_2C)-CH_2-CH_2OH-(CO_2H)$; four bonds in EDTA: $(HO_2C)-CH_2-NR-CH_2-(CO_2H)$, in which R is the remaining part of the molecule). The complexing or chelating agents may comprise one or more molecules containing one or more primary, seconday or tertiary nitrogens within their structure. The complexing or chelating agents may include, but are not limited to, EDTA, citric acid, maleic acid, malic acid, and their salts (which include, but are not limited to, sodium and potassium salts). These agents have been found to be effective in controlling any ion exchange that may be associated with the hydrogel composition. The chelating agents may be present in an amount of from 0.01 to 10% by weight of the prepolymer mixture, preferably from 0.01 to 2% by weight of the prepolymer mixture.

The hydrogel used in the present invention preferably consists essentially of a cross-linked hydrophilic polymer of a hydrophilic monomer and optionally one or more comonomer, together with water and/or one or more organic plasticiser, and optionally together with one or more additives selected from surfactants, polymers, pH regulators, electrolytes, osmolites, chloride sources, bioactive compounds and mixtures thereof, with less than about 40%, for example less than about 10%, by weight of other additives.

For further details of suitable hydrogel material for use in the present invention, and its preparation, please refer to the following publications: PCT Patent Applications Nos. WO-97/24149, WO-97/34947, WO-00/06214, WO-00/06215, WO-00/07638, WO-00/46319, WO-00/65143 and WO-01/96422, the disclosures of which are incorporated herein by reference.

The water activity, which is related to the osmolarity and the ionic strength of the precursor solution (as measured, for example, by a chilled mirror dewpoint meter, Aqualab T3) is preferably between 0.05 and 0.99, more preferably between, 0.2 and 0.99, and even more preferably between 0.3 and 0.98, for example between 0.6 and 0.89. The ionic strength of the precursor solution can therefore be used to optimise the hydrogel properties.

EXAMPLES

The following non-limiting examples are provided as further illustration of the present invention, but without limitation.

In the following Examples, and throughout this description, parts and percentages are by weight unless otherwise stated.

Example 1

Pre-gel: 23 parts by weight of 58% aqueous solution of the sodium salt of acrylamidomethyl-propanesulphonic acid (NaAMPS, LZ2405 Lubrizol), 32 parts acrylic acid (3-sulphopropyl) ester sodium salt, commonly known as SPA or SPANa (SPA or SPANa is available in the form of a solid from Raschig), 37 parts water, 10 parts glycerol and 0.1 parts of a 1 to 10 (by weight) mixture of Daracure 1173 photoinitiator (Ciba Speciality Chemicals) and IRR280 cross-linker (PEG400 diacrylate, UCB Chemicals).

Example 2

Pre-gel: 23 parts by weight of 58% aqueous solution of the sodium salt of acrylamidomethyl-propanesulphonic acid (NaAMPS, LZ2405 Lubrizol), 32 parts acrylic acid (3-sulphopropyl) ester potassium salt, commonly known as SPA or SPAK (SPA or SPAK is available commercially in the form of a pure solid from Raschig), 37 parts water, 10 parts glycerol and 0.1 parts of a 1 to 10 (by weight) mixture of Daracure 1173 photoinitiator (Ciba Speciality Chemicals) and IRR280 cross-linker (PEG400 diacrylate, UCB Chemicals).

Example 3

Pre-gel: 35 parts by weight of 58% aqueous solution of the sodium salt of acrylamidomethyl-propanesulphonic acid (NaAMPS, LZ2405 Lubrizol), 20 parts acrylic acid (3-sulphopropyl) ester sodium salt, commonly known as SPA or SPANa (SPA or SPANa is available in the form of a solid from Raschig), 37 parts water, 10 parts glycerol and 0.1 parts of a 1 to 10 (by weight) mixture of Daracure 1173 photoinitiator (Ciba Speciality Chemicals) and IRR280 cross-linker (PEG400 diacrylate, UCB Chemicals).

Example 4

Pre-gel: 35 parts by weight of 58% aqueous solution of the sodium salt of acrylamidomethyl-propanesulphonic acid (NaAMPS, LZ2405 Lubrizol), 20 parts acrylic acid (3-sulphopropyl) ester potassium salt, commonly known as SPA or SPAK (SPA or SPAK is available commercially in the form of a pure solid from Raschig), 37 parts water, 10 parts glycerol and 0.1 parts of a 1 to 10 (by weight) mixture of Daracure 1173 photoinitiator (Ciba Speciality Chemicals) and IRR280 cross-linker (PEG400 diacrylate, UCB Chemicals).

Example 5

Pre-gel: 67 parts by weight of 58% aqueous solution of the sodium salt of acrylamidomethyl-propanesulphonic acid (NaAMPS, LZ2405 Lubrizol), 0.5 parts acrylic acid (3-sulphopropyl) ester potassium salt, commonly known as SPA or SPAK (SPA or SPAK is available commercially in the form of a pure solid from Raschig), 20 parts water, 10 parts glycerol and 0.1 parts of a 1 to 10 (by weight) mixture of Daracure 1173 photoinitiator (Ciba Speciality Chemicals) and IRR280 cross-linker (PEG400 diacrylate, UCB Chemicals).

Example 6

Pre-gel: 67 parts by weight of 58% aqueous solution of the sodium salt of acrylamidomethyl-propanesulphonic acid (NaAMPS, LZ2405 Lubrizol), 20 parts water, 10 parts glycerol and 0.1 parts of a 1 to 10 (by weight) mixture of Daracure 1173 photoinitiator (Ciba Speciality Chemicals) and IRR280 cross-linker (PEG400 diacrylate, UCB Chemicals).

The change in specificity of the interaction of these gels with proteins is exemplified below with fibrinogen. The Example gels are immersed in a fibrinogen solution for 22 hours and the concentration of fibrinogen in the supernatant is measured by gel permeation chromatography. A relative decrease in fibrinogen concentration is indicative of an enhanced interaction.

Materials and Methods

Gel Permeation Chromatography

Column: Zorbax GF250 9.4×250 mm 4μ (Agilent Technologies)
Guard: Zorbax DIOL 9.4×15 mm 7μ (Agilent Technologies)
HPLC Solvent Pump: Prostar 230 (Varian)
HPLC Autosampler: Prostar 410 (Varian)
HPLC Detector: Prostar 330 (Varian)
UV Deuterium Lamp (Varian)
Software Varian Star Chromatography Workstation (v 5)

All reagents were used as supplied: HPLC grade methanol and water (Fisher Scientific) and analytical reagent grade Na2HPO4 (Riedel-de-Haen).

Molecular Weight Marker Kit: Kit for Molecular Weights 12,000-200,000, For Gel Permeation Chromatography (Sigma-Aldrich).

Fibrinogen Calcium Saline Solution Preparation

Fibrinogen (0.2-0.27 g, 71% purity, Fluka) was dissolved in calcium saline solution (0.81-0.85 g NaCl and 0.027-0.029 g CaCl2 per 100 g water). The mixture was stirred for half an hour at room temperature to ensure maximum dissolution.

Fibrinogen Solution—Hydrogel Experiment

A piece of hydrogel (0.035-0.06 g) had all detachable liners removed and was inserted into a microcentrifuge tube (1.5 ml, polypropylene) of known tare weight. The weight of the hydrogel was recorded. Fibrinogen calcium saline solution (25 times the weight of the hydrogel) was charged to the tube using a microlitre pipette with pipette tips (200-1000 μl, Fisherbrand®, FB34611), and the weight of solution was recorded. The tube was sealed using the cliplock top. The tube was inverted three times to ensure the hydrogel was not stuck to the vessel walls; if the hydrogel did adhere to the tube then gentle tapping was applied to the outside to release it. All samples were prepared in this way and the start time of each experiment was noted. A blank sample (with no gel) was also prepared in the same manner. The samples were stored in ambient conditions.

After the allotted time period had elapsed (22 hrs), the time of the reaction was recorded. The experiment was stopped by carefully removing the hydrogel from the tube and transferring it to a clean tared microcentrifuge tube (1.5 ml, polypropylene). The weight of the gel was recorded. All experiments were exposed to the gel for the same period of time.

The remaining supernatant was extracted from the microcentifuge tube with a sterile disposable syringe (1.0 ml, polypropylene). A syringe filter (13 mm, 0.2 μm PTFE membrane, PP housing) was attached to the syringe and the mixture was filtered, to remove any solids, into a short thread vial (1.5 ml, amber, Varian). The vial was sealed with a screw cap (polypropylene, Varian).

GPC Calibration

Bovine Serum Albumin (0.01 g, BSA) was dissolved in buffered saline (0.1M NaCl 0.02M Na2HPO4 in 5% methanol/water) and made up to volume in a volumetric flask (25 ml). The protein solution was filtered through a syrninge filter (13 mm, 0.2 μm PTFE membrane, PP housing) into a short thread vial (1.5 ml, amber, Varian). The vial was sealed with a screw cap (polypropylene, Varian).

The BSA solution (25 μl) was injected into the HPLC with an autosampler. The HPLC conditions were as follows:

Column: Zorbax GF250 9.4×250 mm 4μ (Agilent Technologies)
Guard: Zorbax DIOL 9.4×15 mm 7μ (Agilent Technologies)
Mobile Phase: 0.2M Na2HPO4 in 5% methanol/water
Flow rate: 0.8 ml·min-1
Run time: 30 mins
Temp: 30° C.
Detector wavelength: 215 nm Molecular weight markers from the Kit for Molecular Weights 12,000-200,000 (Sigma-Aldrich) were prepared in the same manner as the BSA solution, using the following concentrations: Cytochrome C (0.0037 g in 25 ml); Carbonic Anhydrase (0.0057 g in 25 ml); Alcohol dehydrogenase (0.0058 g in 25 ml); β-amylase (0.0046 g in 25 ml).

GPC on Protein Samples

Fibrinogen solutions were prepared as described earlier and analysed by gel permeation chromatography using the conditions outlined earlier in this document.

Chromatographic Analysis

Peak height and peak area determination was performed with Varian Star Chromatography Workstation (v 5) software package.

Results

See Tables 1 to 6 below and FIGS. 1 to 3 for results and graphs based thereon:

Table 1 shows molecular weight markers and retention time data in the gel permeation chromatography test, as described above.

| Mw Markers | | | | |
|---|---|---|---|---|
| Molecule | Mw | $Log_{10}Mw$ | Rt | Ve/V0 |
| Blue Dextran | 2000000 | 6.30 | 9.34 | 1.00 |
| Bovine Serum Albumin | 66430 | 4.82 | 11.49 | 1.23 |
| Cytochrome C | 12400 | 4.09 | 15.20 | 1.63 |
| Carbonic Anhydrase | 29000 | 4.46 | 13.50 | 1.45 |
| Alcohol Dehydrogenase | 150000 | 5.18 | 11.07 | 1.19 |
| β-amylase | 200000 | 5.30 | 10.65 | 1.14 |

FIG. 1 shows the results of Table 1 in a graph of retention time (mins) versus Log 10 molecular weight.

Table 2 shows results for peak area versus concentration test. Linearity (Peak Area).

Validation: Linearity (Fibrinogen)

| Peak Area | | | |
|---|---|---|---|
| [Fibrinogen]/ g/ml | Mean Area | STDEV | Samples |
| 0.000229 | 1.44E+07 | 3.01E+06 | 5 |
| 0.001016 | 7.21E+07 | 7.66E+06 | 6 |
| 0.001751 | 1.28E+08 | 5.14E+06 | 6 |
| 0.002052 | 1.56E+08 | 2.46E+06 | 5 |
| 0.003272 | 2.43E+08 | 2.15E+06 | 3 |

FIG. 2 shows the results of Table 2 in a graph of peak area (units) versus fibrinogen concentration (g/ml). Error bars are standard deviation.

Table 3 shows linearity for peak area versus concentration for fibrinogen:

| Linearity (Peak Area) | | |
|---|---|---|
| $R^2 = 0.999$ | $y_0 = -3.25e^6$ | $m = 5.4e^{10}$ |

Table 4 shows results for peak height versus concentration test for fibrinogen:

| Peak Height | | | |
|---|---|---|---|
| [Fibrinogen]/g/ml | Mean Area | STDEV | Samples |
| 0.000229 | 7.96E+04 | 2.01E+04 | 5 |
| 0.001016 | 4.63E+05 | 5.63E+04 | 6 |
| 0.001751 | 8.89E+05 | 4.95E+04 | 6 |
| 0.002052 | 1.12E+06 | 2.64E+04 | 5 |
| 0.003272 | 1.90E+06 | 3.66E+04 | 3 |

Table 5 shows results for peak height linearity for fibrinogen:

| Linearity (Peak Height) | | |
|---|---|---|
| $R^2 = 0.995$ | $y_0 = -1.15e^5$ | $m = 6.04e^8$ |

Table 6: Table 6 shows the fibrinogen concentration in an aqueous calcium saline solution after 24hrs exposure to a hydrogel totally immersed in the fibrinogen solution.

| GEL | [Fibrinogen] g/100 ml | Average [Fib] g/100 ml | Replicate STDEV | Replicate Variance |
|---|---|---|---|---|
| Example 1 | 2.66E-03 7.05E-03 | 0.005 | 3.10E-03 | 9.61E-06 |
| Example 2 | 7.87E-02 1.09E-01 | 0.094 | 2.15E-02 | 4.61E-04 |
| Example 3 | 1.44E-02 3.79E-02 | 0.026 | 1.66E-02 | 2.77E-04 |
| Example 4 | 1.18E-01 1.29E-01 | 0.123 | 7.38E-03 | 5.44E-05 |
| Example 5 | 1.30E-01 1.31E-01 | 0.130 | 2.50E-04 | 6.26E-08 |
| Example 6 | 1.08E-01 1.28E-01 | 0.118 | 1.40E-02 | 1.96E-04 |

FIG. 3 shows the results from Table 6 in a chart of fibrinogen concentration in supernatant fluid (g/100 ml) after 22 hrs exposure to six different hydrogels of Examples 1 to 6.

The high degree of linearity in both the peak area vs concentration test and the peak height vs concentration test indicates that either peak area or peak height, as measured on a calibrated HPLC apparatus, may reliably be used to determine the concentration of fibrinogen in solution.

The data in Table 6 and FIG. 3 clearly show that enhanced interaction with fibrinogen is obtained when a high concentration of NaSPA is used relative to the co-monomer, NaAMPS. It appears that hydrogels of Examples 1 and 3 were surprisingly able to absorb more fibrinogen than the hydrogels of the other Examples. The corresponding KSPA, NaAMPS copolymers do not show the enhanced interaction. These data clearly demonstrate the importance of both the anion and counter cation in the hydrogel polymers for controlling interactions with proteins.

The present invention provides an effective method of inhibition of inflammation, useful for example (but not exclusively) in the treatment of wounds, for example chronic skin lesions such as ulcerated skin lesions (e.g. chronic venous or arterial leg ulcers) to promote their healing.

In the context of the treatment of wounds, the method makes available inhibition of inflammation and/or the complement cascade and/or the kinin cascade, and potentially simultaneous reduction of one or more undesirable characteristics of a wound, for example a chronic skin lesion, selected from pain associated with the wound, pain associated with changing of the dressing, exudation, malodour, irritation and hyperkeratosis, as has already been described in our PCT patent application No. PCT/GB2006/002632 (WO2007/007115).

Undesirable effects of conventional dressings for wounds such as chronic skin lesions, for example maceration, incomplete absorption of exudate, excoriation, scarring of the final healed tissue, contact dermatitis, varicose eczema or skin stripping can also be reduced using the present invention in the context of wound treatment.

The hydrogel (dressing) used in the present invention is easy to apply and change, with resultant cost savings and efficiency enhancements.

The above broadly describes the present invention, without limitation. Variations and modifications as will be readily apparent to those of ordinary skill in this art are intended to be covered by this application and all subsequent patents.

The invention claimed is:
1. A hydrogel composition for the treatment of wounds, comprising a hydrophilic copolymer carrying multiple pendant sulphonic groups, wherein the copolymer is derived from a first olefinically unsaturated sulphonic acid monomer and a second olefinically unsaturated sulphonic acid ester monomer, wherein both monomers have an octanol:water partition coefficient (LogP) value of less than 0, wherein the first monomer has a LogP value greater (more positive) than the second monomer, the molar ratio of the first monomer/second monomer in the hydrogel is between 1 to 3, and both the first and second monomers comprise a pendant sulphonic group in salt form and the counterion for both monomers is sodium, and wherein the first monomer is acrylic acid (3-sulphopropyl) ester (NaSPA) and the second monomer is 2-acrylamido-2-methylpropanesulphonic acid (NaAMPS).

2. A hydrogel composition according to claim 1, wherein the molar ratio of the first monomer/second monomer in the hydrogel is between 2 to 3.

3. A hydrogel composition according to claim 1, wherein the molar ratio of the first monomer/second monomer in the hydrogel is between 2.4 to 3.

* * * * *